US007217800B2

(12) United States Patent
Takasaki et al.

(10) Patent No.: US 7,217,800 B2
(45) Date of Patent: May 15, 2007

(54) PEPTIDE LEUKOTRIENE RECEPTOR

(75) Inventors: Jun Takasaki, Tsukuba (JP); Masazumi Kamohara, Tsukuba (JP); Mitsuyuki Matsumoto, Tsukuba (JP); Tetsu Saito, Tsukuba (JP); Tohru Sugimoto, Tokyo (JP); Toshio Ota, Fujisawa (JP); Takao Isogai, Ami-machi (JP); Tetsuo Nishikawa, Tokyo (JP); Yuri Kawai, Kisarazu (JP)

(73) Assignees: Astellas Pharma Inc., Tokyo (JP); Helix Research Institute, Chiba (JP)

( * ) Notice: Subject to any disclaimer, the term of this patent is extended or adjusted under 35 U.S.C. 154(b) by 161 days.

(21) Appl. No.: 10/932,004

(22) Filed: Sep. 2, 2004

(65) Prior Publication Data

US 2005/0037968 A1   Feb. 17, 2005

Related U.S. Application Data

(62) Division of application No. 09/979,603, filed as application No. PCT/JP00/06265 on Sep. 13, 2000, now Pat. No. 6,878,525.

(30) Foreign Application Priority Data

Sep. 14, 1999   (JP) ................. 11-259986

(51) Int. Cl.
*C07K 16/28*   (2006.01)
(52) U.S. Cl. .............. 530/388.22; 530/387.9; 424/143.1
(58) Field of Classification Search ............... None
See application file for complete search history.

(56) References Cited

U.S. PATENT DOCUMENTS 5,011,912 A * 4/1991 Hopp et al. ............ 530/387.9

FOREIGN PATENT DOCUMENTS

| WO | WO 01/36471 A2 | 5/2001 |
| WO | WO 01/42269 A1 | 6/2001 |
| WO | WO 01/59105 A1 | 8/2001 |
| WO | WO 01/59118 A1 | 8/2001 |
| WO | WO 01/94580 A1 | 12/2001 |

OTHER PUBLICATIONS

Harvey et al. Mouse Monoclonal Antibody to a Latent Epitope of Leucocyte Receptors for Leukotriene B4, May 1992, Immunology 76(1):122-128.*

European Search Report dated Dec. 12, 2005, for EP-05-01-8471.
Koshino T. et al: "Effect of a $Ca^{2+}$ antagonist, nifedipine, on the experimental asthma mediated mainly by slow reacing substance of anaphylaxis." Arzneimittel-Forshung, vol. 35, No. 8, 1985, pp. 1231-1236.
Yamamoto H. et al: "Inhibition of analgestic-induced asthma by leukotriene receptor antagonist ONO-1078", American Journal of Respiratory and Critical Care Medicine, vol. 150, No. 1, Jul. 1994, pp. 254-257.
Cauvin C. et al: "Mechanisms of calcium antagonist-induced vasodilation.", Annual Review of Pahrmacology and Toxicology, vol. 23, 1983, pp. 373-396.
Ooaki R. et al: "Therapeutic Effect of Pranlukast, a Selective Cysteinyl Leukotriene Receptor Antagonist, on Bronchial Asthma", International Archives of Allergy and Immunology, vol. 114, No. 1, 1997, pp. 97-100.
Kreutner W. et al: "The effect of leukotrine antagonists, lipoxygenase inhibitors and selected standards on leukotriene allergic bronchospasm in guinea pigs", Agents and Actions, vol. 28, No. 3-4, 1989, pp. 173-184.
Snyder D. W. et al: Leukotriene receptor antagonists as potential therapeutic agents., Annual Review of Pharmacology and Toxicology, vol. 29, 1989, pp. 123-143.
Jones T. R. et al: "L-649,923, Sodium Betta-S Gamma-R-4-3-4 Acetyl-3-Hydroxy-2-propylphenoxy Propylthio-Gamma-Hydroxy-Beta-Methylbenzenebutanoate, a selective, orally active leukotriene receptor antagonist", Canadian Journal of Physiology and Pharmacology, vol. 64, No. 8, 1986, pp. 1068-1075.
J. Takasaki et al., Biochemical and Biophysical Research Communications 274, 316-322 (2000) "The Molecular Characterization and Tissue Distribution of the Human Cysteinyl Leukotriene $CysLT_2$ Receptor".
C.E. Heise et al. The Journal of Biological Chemistry vol. 275, No. 39, Issue of Sep. 29, pp. 30536 (2000) "Characterization of the Human Cysteinyl Leukotriene 2 Receptor".
Dahlen S.E., Leukotriene Receptors, *Clin. Rev. Allergy Immunol.*, 17 (1-2): 179-191 (1999).
Yokomizo et al. A G-protein-coupled receptor for leukotriene B4 that mediates chemotaxis. Jun. 5, 1997, Nature 387:620-624.
Kaplan et al., Identification of a G Protein coupled Receptor Induced in Activated T Cells. Jul. 15, 1993, J. Immunol. 151-628-636.

* cited by examiner

*Primary Examiner*—John Ulm
(74) *Attorney, Agent, or Firm*—Sughrue Mion, PLLC

(57)   ABSTRACT

A cDNA encoding a novel $LTC_4$ receptor has been isolated. Provision of the novel protein, an $LTC_4$ receptor, enabled binding experiments using the $LTC_4$. By screening for compounds that modulate $LTC_4$ receptor activity based on these binding experiments, development of drugs targeting the $LTC_4$ receptor becomes possible.

1 Claim, 8 Drawing Sheets

Figure 8
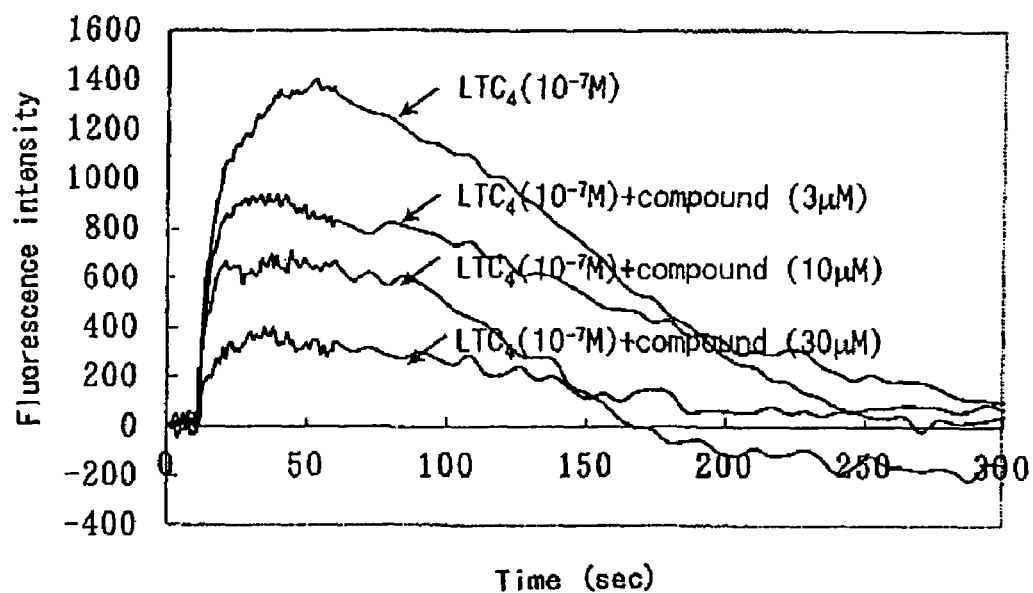
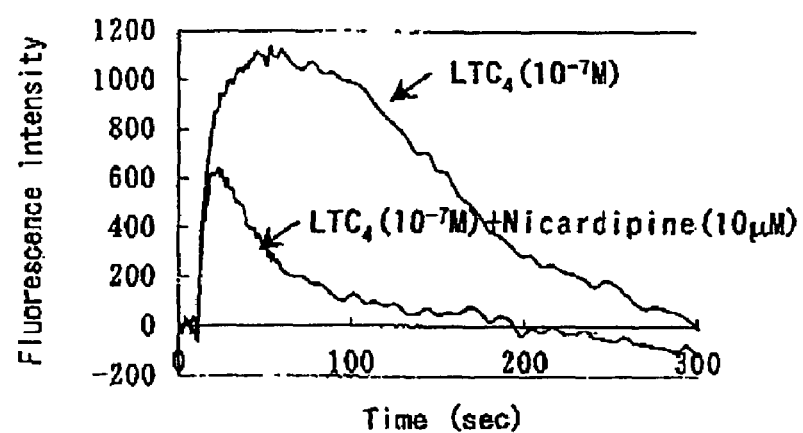

PEPTIDE LEUKOTRIENE RECEPTOR

This is a divisional of U.S. application Ser. No. 09/979,603 filed Jul. 29, 2002 now U.S. Pat. No. 6,878,525, which is a National Stage Under 35 U.S.C. § 371 of PCT/JP00/06265 filed Sep. 13, 2000.

TECHNICAL FIELD

The present invention relates to novel peptide leukotriene receptor proteins, DNA encoding the novel proteins, vector which contains the DNA, transformed cells which contain the vector, and methods for screening drugs using the transformed cells.

BACKGROUND ART

Eicosanoids, such as prostaglandin, thromboxanes, and leukotrienes, are one of the families of metabolites of arachidonic acid. To maintain homeostasis of the living body, eicosanoids show various physiological effects (see "Koza prostaglandin 1–8", Makoto Katori, Seiitsu Murota, Shozo Yamamoto Ed. (1988)). These physiological effects purportedly appear through a specific cell membrane receptor of each eicosanoid. Leukotrienes, one of the eicosanoids, are a series of physiologically active lipids that show a strong physiological activity at low concentrations among the metabolites of arachidonic acid in the 5-lipoxygenase pathway (Samuelsson, B. et al. (1987) Science. 237, 1171–1176).

Leukotrienes are divided roughly into two kinds, namely leukotriene B4 ($LTB_4$) and the peptide leukotriene in which peptides are bound to fatty acids. Leukotriene C4 ($LTC_4$), leukotriene D4 ($LTD_4$), and leukotriene E4 ($LTE_4$) are examples of the latter peptide leukotrienes. The $LTB_4$ is a strong activator of leukocytes, and plays important roles in inflammatory immune reaction, infection protection, and the like (Chen, X. S. et al. (1994) Nature 372. p179–182). On the other hand, $LTC_4$, $LTD_4$, and $LTE_4$ have actions such as contraction of various smooth muscles (including the airway smooth muscle) stimulation of the mucos secretion in the airway, constriction of arteriolae and venule, and edudation of plasma protein (Taylor, G. W. et al. (1986) Trends Pharmacol. Sci. 7, p100–103). Therefore, it is thought that the peptide leukotriene is involved in the crisis, ingravescent, exacerbation of inflammation and allergic symptoms, for instance, respiratory diseases such as asthma, bronchitis, and allergic rhinitis, dermatosis such as psoriasis and dermatitis, and intestinal diseases such as inflammatory bowel disease and ulcerative colitis (Makoto Katori, Seiitsu Murota, Shozo Yamamoto Ed. (1988) "Koza prostaglandin 3", 225–227, 484–486; Piper, P. J. et al., (1984) Physiol. Rev. 64. 744–761; Taylor, G. W. et al. (1986) Trends Pharmacol. Sci. 7. 100–103; Lewis, R. A. et al. (1990) N. Engl. J. Med. 323. 654–655). Moreover, it is known that the peptide leukotrienes, $LTC_4$ and $LTD_4$, cause a prominent decrease in cardiac contractivity and the coronary flow (Makoto Katori, Seiitsu Murota, Shozo Yamamoto Ed. (1988) "Koza prostaglandin 2", 64–70; Piper, P. J. et al. (1984) Physiol Rev. 64. 744–761; Letts, L. G. et al., (1982) Br. J. Pharmacol. 76, 169–176; Chiono, M. et al., (1991) J. Pharmacol. Exp. Ther. 256, 1042–1048), and thus the relation of peptide leukotriene to cardiovascular disturbance is pointed out.

Taken together, it is thought that clarifying the structure and the characteristics of the receptor of leukotrienes would lead to elucidation of the physiological role of leukotrienes, and consequently, to elucidation of diseases related to leukotrienes, discovery of methods of medical treatment, and so on.

To date, according to the IUPHAR (International union of Pharmacology), receptors of leukotrienes are classified pharmacologically into three types, namely the BLT receptor, CysLT1 receptor, and CysLT2 receptor, (Alexander, S. P. H. et al., (1997) Trends Pharmacol. Sci. (Suppl.) 50–51).

The BLT receptor specifically recognizes the $LTB_4$. The CysLT1 receptor and CysLT2 receptor both recognize peptide leukotrienes. The biological action of the CysLT2 receptor is not blocked by existing classical $LTD_4$ receptor antagonists (ICI204219, MK476, SR2640, SKF104353, and LY170680, etc.) while that of the CysLT1 receptor is. The existence of additional peptide leukotriene receptor, apart from the CysLT1 receptor and the CysLT2 receptor, has been proposed (Jonsson, E. W. et al. (1998) Eur. J. Pharmacol. 357, 203–211).

The BLT receptor genes have been isolated and identified in both human (Yokomizo, T. et al. (1997) Nature 387. 620–624) and mouse (Martin, V. et al. (1999) J. Biol. Chem. 274. 8597–8603). Likewise, human CysLT1 receptor has been recently isolated and identified, and it turned out that $LTD_4$ is a high affinity ligand thereto (Lynch, K. R. et al. (1999) Nature 399, 789–793). However, receptors of peptide leukotrienes, especially genes of receptors with a high affinity to $LTC_4$ other than the CysLT1 receptor, have not been isolated and identified in any species until now.

In addition, antagonists of the BLT receptor (Negro, J. M. et al. (1997) Allergol. Immunopathol. Madr. 25, 104–112; Kishikawa, K. et al. (1995) Adv. Prostaglandin Thromboxane Leukot Res. 23, 279–281) and antagonists of the CysLT1 receptor (Leff, J. A. et al. (1998) N. Engl. J. Med. 339, 147–152; Suisa, S. et al. (1997) Amm. Int. Med. 126, 177–183; Grossman, J. et al. (1997) J. Asthma 34, 321–328) have been researched and developed, aiming at antiphlogistic drug.

On the other hand, among the leukotriene receptors, research and development of antagonists and agonists of the receptors with a high affinity especially to $LTC_4$ has been remained behind (Gardiner, P. J. et al. (1994) Adv. Prostaglandin Thromboxane Leukot. Res. 22, 49–61; Capra, V. et al. (1998) Mol. Pharmacol. 53, 750–758). The main cause is that the binding of $LTC_4$ to the receptor is masked by low affinity-$LTC_4$ binding proteins, such as glutathione S-transferase and $LTC_4$ synthase, which exist in cells and the tissues, so that binding experiments using cells and tissue preparations are difficult to conduct. Therefore, provision of a $LTC_4$ receptor which enables binding experiments to be performed in vitro is needed in the art.

DISCLOSURE OF THE INVENTION

The subject of the present invention is to provide a human $LTC_4$ receptor or a protein with a function equivalent thereto and genes encoding same. A further object of the present invention is to provide a method of screening for a compound useful as a medicine targeting the peptide leukotriene receptor using the $LTC_4$ receptor protein.

The present inventors considered that the human full-length cDNA library might be useful in the isolation of DNA encoding the $LTC_4$ receptor. To date, the isolation of the $LTC_4$ receptor protein has not been accomplished though it was desired. Therefore, there is a need to try a quite new approach. In particular, it was considered that the isolation of an unknown protein could be expeditiously identified by using a full-length cDNA library, which surely contains the protein-coding region. This is because the function of the protein can be easily confirmed by transfecting the full-length cDNA with the translational initiation codon into cells.

First, the present inventors synthesized a human cDNA library with a high full-length rate using the oligo cap method (K. Maruyama and S. Sugano, Gene, 138: 171–174 (1994); Y. Suzuki et al., Gene, 200: 149–156 (1997)). Then, the human full-length cDNA was cloned from the clone isolated from the cDNA library. Further, to select cDNA presumed to encode a membrane receptor, cDNA clones encoding the amino acid sequence comprising the signal sequence or the transmembrane domain were selected from the full-length cDNA clones. Among the cDNA clones thus selected, a cDNA encoding a protein with leukotriene C4 ($LTC_4$) receptor activity was identified by the transformation into COS cells. In addition, it was found out that the protein encoded by the cDNA enables the screening for compounds that modify the activity of the $LTC_4$ receptor. In addition, pig and rat homologues of this cDNA were isolated, and it was determined that both encode a protein with $LTC_4$ receptor activity. Moreover, the present inventors discovered that the receptors of the present invention have not only the $LTC_4$ receptor activity but also simultaneously a $LTD_4$ receptor activity, and completed the present invention.

In particular, the present invention relates to the following proteins, DNA encoding the proteins, and the use of same.

(1) A protein with leukotriene C4 receptor activity, comprising an amino acid sequence of any one of SEQ ID NO: 2, 18, and 22, or amino acid sequence of any one of SEQ ID NO: 2, 18, and 22, wherein one or more amino acid(s) in the sequence is modified by deletion, addition, insertion and/or substitution by other amino acids;

(2) a protein with leukotriene C4 receptor activity, encoded by a DNA which hybridizes under stringent conditions to a DNA consisting of the nucleotide sequence of any one of SEQ ID NO: 1, 17, and 21;

(3) a DNA encoding the protein of (1) or (2);

(4) a transformant carrying the DNA of (3) in an expressible manner;

(5) a method for producing the protein of (1) or (2), comprising the steps of culturing the transformant of (4), and recovering the expressed product;

(6) an antibody against the protein of (1) or (2);

(7) a method for detecting the ability of a test compound to modulate leukotriene C4 receptor activity, comprising the steps of:

(a) contacting a test compound with the protein of (1) or (2), or transformed cells expressing said protein, under the existence of a ligand for leukotriene C4 receptor, and (b) measuring changes in leukotriene C4 receptor activity;

(8) a method of screening for a compound which modulates leukotriene C4 receptor activity, comprising the steps of:

(a) contacting a test compound with the protein of (1) or (2), or transformed cells expressing said protein, under the existence of a ligand for leukotriene C4 receptor, (b) measuring changes in leukotriene C4 receptor activity, and (c) selecting the compound that modulates leukotriene C4 receptor activity;

(9) a pharmaceutical composition for anti-inflammation or anti-allergy, comprising an antagonist of a protein having leukotriene C4 receptor activity described in (1) or (2) and pharmaceutically acceptable additive; and

(10) a pharmaceutical composition for vasodilation comprising an antagonist of a protein having leukotriene C4 receptor activity described in (1) or (2) and pharmaceutically acceptable additive.

Further, the present invention relates to the use of antagonists of proteins having leukotriene C4 receptor activity described in (1) or (2) in manufacturing a pharmaceutical composition for anti-inflammation, anti-allergy, and vasodilation, such pharmaceutical compositions comprising antagonist and pharmaceutically acceptable additive.

In addition, the present invention relates to the antagonists of proteins having leukotriene C4 receptor activity described in (1) or (2), which can be obtained by the screening method described in (8). Additionally, the present invention relates to the use of compounds that can be obtained by the screening method described in (8), as an antagonist of proteins having leukotriene C4 receptor activity described in (1) or (2).

The present invention relates to the $LTC_4$ receptor protein. The protein of the present invention is encoded by a cDNA selected from the clones of the full-length cDNAs constituting the full-length cDNA library. Moreover, the protein of the present invention is a pig or rat homologue isolated based on the nucleotide sequence information of the human full-length cDNA disclosed in the present invention. According to the search result in the GenBank and SwissProt, the nucleotide sequence (about 2.8 kb) shown in SEQ ID NO: 1 and the deduced amino acid sequence (SEQ ID NO: 2, 346 amino acid residues) encoded by the nucleotide sequence are novel. Moreover, the amino acid sequences of the pig and rat homologues of this protein and the nucleotide sequences encoding same are also novel. The amino acid sequence of the protein derived from pig is shown in SEQ ID NO: 18, and the nucleotide sequence of the corresponding cDNA is shown in SEQ ID NO, 17. Moreover, the amino acid sequence of the protein derived from rat is shown in SEQ ID NO: 22, and the nucleotide sequence of the corresponding cDNA is shown in SEQ ID NO: 19. The amino acid sequence of the $LTC_4$ receptor protein of the present invention showed a homology of 31% and 20% to well-known human CysLT1 receptor and human BLT receptor, respectively. On the other hand, comparison of proteins derived from pig and rat with the human protein revealed structural similarities as follows.

|  | Amino acid residue | Homology to human |
|---|---|---|
| Human | 346 | — |
| Pig | 345 | 77.7% |
| Rat | 309 | 72.6% |

The $LTC_4$ receptor activity of the proteins derived from pig and rat was confirmed as well as in the protein of the present invention. Based on these facts, it was considered that both of these proteins isolated in the present invention were homologues of the human $LTC_4$ receptor. The proteins of the present invention and genes thereof, and compounds modulating the activity of proteins of the present invention, can be applied to the prevention and treatment of diseases in which $LTC_4$ and the receptors are involved.

As mentioned above, it is considered that peptide leukotrienes such as $LTC_4$ and $LTD_4$ are involved in the crisis, ingravescent, exacerbation of respiratory diseases such as asthma, bronchitis, or allergic rhinitis; dermatosis such as psoriasis and dermatitis; intestinal diseases such as inflammatory bowel disease and ulcerative colitis; and the like. Moreover, peptide leukotrienes ($LTC_4$ and $LTD_4$) have been shown to be relevant to cardiovascular disturbances Therefore, the $LTC_4$ receptor provided by the present invention is considered to play an important role in these diseases and their symptoms. Therefore, compounds modifying the activity of the $LTC_4$ receptor are useful as pharmaceuticals for the treatment and/or prevention of these diseases. For instance, a compound that interferes with the binding between $LTC_4$ receptor and $LTC_4$ and does not stimulate to the $LTC_4$ receptor, acts as an antagonist (blocker) of $LTC_4$. Such a compound is useful in the treatment and the prevention of diseases mediated by the $LTC_4$ receptor Moreover, since receptors of the present invention have the $LTD_4$ receptor activity, the antagonist of present receptors acts as an antagonist of the $LTD_4$ receptor. Therefore, it can be a better medicine for the remedy and prevention of diseases in which both of above-mentioned $LTC_4$ and $LTD_4$ are involved.

The protein of the present invention can be prepared as a recombinant protein or a natural protein. The recombinant protein can be prepared by, for instance, transfecting into a suitable host cell a vector in which the DNA of the present invention is inserted, and purifying the protein expressed in the transformant as described below. Alternatively, it is also possible to prepare the protein of the present invention by in vitro translation (see for example, "On the fidelity of mRNA translation in the nuclease-treated rabbit reticulocyte lysate system. Dasso, M. C., Jackson, R. J. (1989) NAR 17: 3129–3144") or the like. On the other hand, the natural protein can be prepared using an affinity column, which conjugates antibodies against the protein of the present invention described below (Current Protocols in Molecular Biology edit. Ausubel et al. (1987) Publish. John Wiley & Sons Section 16.1–16.19). The antibodies to be used for affinity purification may be either monoclonal antibodies or polyclonal antibodies.

The present invention includes not only the protein of the amino acid sequence of SEQ ID NO: 2, but also the proteins "functionally equivalent" to the protein comprising the amino acid sequence of SEQ ID NO: 2, wherein one or more amino acid is modified by deletion, addition, insertion and/or substitution with other amino acids. "Functionally equivalent" means that the object protein has an equivalent biological characteristic to the protein of SEQ ID NO: 2. The biological characteristic of interest of the protein of SEQ ID NO: 2 is its ability to function as the receptor of $LTC_4$s. In the present invention, $LTC_4$ receptor activity is defined as an activity to have binding affinity to $LTC_4$ and increase intracellular $Ca^{++}$ concentration in a $LTC_4$ dose-dependent manner by the binding of $LTC_4$. In the present invention, a certain protein can be described as having binding affinity to $LTC_4$, when it shows a high binding affinity with a dissociation constant preferably Kd=30 nM or less, more preferably Kd=5 nM or less.

In addition, proteins with equivalent biological characteristic to protein of the present invention preferably also have $LTD_4$ receptor activity. $LTD_4$ receptor activity is defined as an activity to have a binding affinity to $LTD_4$ and to increase the intracellular $Ca^{++}$ concentration in a $LTD_4$ dose-dependent manner by the binding of $LTD_4$.

There is no limitation on the number of mutations and mutation sites of amino acid in the protein, so long as the functions are retained. The number of mutations is typically no more than 10%, preferably no more than 5%, more preferably no more than 1%, of all amino acids.

A partial peptide fragment of the protein of the present invention can be obtained based on the present invention. For instance, a partial peptide fragment which has a binding affinity for the ligand and functions as a competitive inhibitor of the protein of the present invention can be provided. Likewise, an antigen peptide for antibody preparation can be obtained. Partial peptide fragments consist of amino acid sequence selected from at least 7, preferably 8 or more, more preferably 9 or more continuous amino acids of the amino acid sequence described in SEQ ID NO: 2, so that they are specific to the protein of the present invention. In addition to the preparation of antibodies against the protein of the present invention and competitive inhibitors of the protein of the present invention, the partial peptide fragments of the present invention can be used in the screening of ligands which bind to the protein of the present invention, and so on. A partial peptide fragment of the present invention can be produced, for instance, by a genetic engineering technique, well-known peptide synthesis methods, or by digesting the protein of the present invention by a suitable peptidase.

Moreover, the present invention relates to DNAs encoding the above-mentioned proteins of the present invention. As a DNA of the present invention, genomic DNA and chemosynthetic DNA and the like as well as cDNA are included, with no special limitation to its form so long as it can encode the protein of the present invention. Moreover, in light of the degeneracy of the genetic code, a DNA with any nucleotide sequence is included in the present invention so long as it can encode a protein of the present invention. For instance, such nucleotide sequences can be determined according to conventional methods, in the consideration of the codon usage of the host (Crantham, R. et al. (1981) Nucleic Acids Res., 9, r43–r74). Furthermore, a portion of the codons of these nucleotide sequences can be modified by site specific mutagenesis (Mark, D. F. et al. (1984) Proc. Natl. Acad. Sci. USA, 81, 5662–5666), using primers which consist of synthetic oligonucleotides encoding the desired alteration, and the like.

The DNA of the present invention can be isolated by conventional methods, such as the hybridization method, using the DNA sequence (SEQ ID NO: 1) encoding the protein comprising SEQ ID NO: 2 or a portion thereof as probes, or the PCR method, using primers synthesized based on the DNA sequences. For instance, a cDNA may be synthesized using mRNA extracted from human cells or tissues capable of producing an $LTC_4$ receptor protein of the present invention as the template, and then be integrated into a vector to prepare a cDNA library. For example, human spleen can be used as the cells or tissues which have the ability to produce the $LTC_4$ receptor of the present invention. By screening the library by colony hybridization or plaque hybridization using probes designed based on SEQ ID NO: 1, the objective cDNA can be cloned.

Moreover, one skilled in the art can generally isolate a DNA having a high homology with the nucleotide sequence (SEQ ID NO: 1) encoding the protein consisting of SEQ ID NO: 2 or parts thereof, using conventional hybridization techniques (Current Protocols in Molecular Biology edit. Ausubel et al. (1987) Publish. John Wiley & Sons Section 6.3–6.4), and can thereby obtain a DNA encoding a protein functionally equivalent to the protein of the present invention. Such a DNA obtained in this manner is included in the present invention.

Example organisms that may be used to isolate a gene encoding functionally equivalent protein include rat, mouse, rabbit, chicken, pig, and cattle as well as human, but are not limited as such.

The stringency of hybridization required to isolate a DNA encoding a functionally equivalent protein is normally "1×SSC, 0.1% SDS, 37° C." or so, a more stringent condition being "0.5×SSC, 0.1% SDS, 42° C." or so, and a much more stringent condition being "0.2×SSC, 0.1% SDS, 65° C."or so as a washing condition. As the stringency becomes higher, isolation of a DNA with higher homology to the probe sequence can be expected. However, above-mentioned combinations of conditions of SSC, SDS, and temperature are only an exemplification and one skilled in the art can achieve the same stringency as described above by appropriately combining above-mentioned factors or other (for example, probe concentration, probe length, reaction time of hybridization, etc.) which determine the stringency of the hybridization.

The proteins encoded by the DNA of the present invention isolated by using such hybridization techniques normally have high homology in their amino acid sequences to the protein of SEQ ID NO: 2. High homology indicates a sequence identity of at least 60% or more, desirably 70% or more. In a preferred embodiment, high homology refers to a sequence identity of 90% or more, more preferably 95% or more, further more preferably 99% or more. Homology can be determined by using the BLAST search algorithm.

Moreover, using gene amplification techniques (PCR) (Current protocols in Molecular Biology edit. Ausubel et al. (1987) Publish. John Wiley & Sons Section 6.1–6.4), DNA fragments having high homology with the DNA sequence or parts thereof, which encodes the protein consisting of SEC ID NO: 2, can be also isolated by designing primers based on the portion of the DNA sequence encoding the protein consisting of SEQ ID NO: 2 (i.e., SEQ ID NO: 1).

DNA of the present invention are finally isolated by confirming the $LTC_4$ receptor activity of the obtained proteins encoded by the DNA consisting of the nucleotide sequence having high homology to the nucleotide sequence of SEQ ID NO: 1. The $LTC_4$ receptor activity can be identified by transforming animal cells with cDNA to be translated to proteins, and then screening them for the binding of antibodies or $LTC_4$ to $LTC_4$ receptors as an index. In addition to animal cells, in vitro translation can be used for the translation of the protein.

The present invention includes proteins thus isolated and DNAs encoding them. Namely, the present invention provides a DNA indicated in SEQ ID NO: 17 and the $LTC_4$ receptor derived from pig consisting of the amino acid sequence (SEQ ID NO: 18) encoded by the DNA. Further, the present invention provides a DNA described in SEQ ID NO: 21 and the $LTC_4$ receptor derived from rat consisting of the amino acid sequence (SEQ ID NO: 22) encoded by the DNA.

It is generally considered that eukaryotic genes show polymorphism, as known in interferon genes (see, for example, Nishi, T. et al. (1985) J. Biochem., 97, 153–159), and such. One or more amino acid(s) may be substituted by the polymorphism, or the amino acid sequence may not be changed at all through the nucleotide sequence changes. The DNA with mutation in the nucleotide sequence based-on these polymorphisms are included in the DNA of the present invention.

Chemosynthetic DNA can be synthesized by using a DNA synthesizer (for instance, Oligo 1000M DNA Synthesizer (Beckman) or 394 DNA/RNA Synthesizer (Applied Biosystems), and so on). Methods for synthesizing DNAs chemically are well-known and include, for example, the phosphite triester method (Hunkapiller, M. et al. (1984) Nature, 10, 105–111).

The present invention further relates to vectors in which the DNA of the present invention are inserted. The vector of the present invention is not limited, so long as it can stably carry the inserted DNA. For instance, vectors such as pBluescript (Stratagene), and the like are preferred cloning vectors when using E. coli as the host. If the vector is to be used for the purpose of producing proteins of the present invention, expression vectors are especially useful. The expression vector is not limited so long as it expresses the protein of interest in vitro, in E. coli, in culture cells, and in vivo. For instance, the pBEST vector (Promega) is known for in vitro expression and the pET vector (Invitrogen) is known for E. coli. For vertebrate cells, an expression vector having a promoter located upstream to the gene to be expressed, as well as an RNA splice site, a polyadenylation site, a transcriptional termination signal, and the like can be generally used. If necessary, the expression vector may also have an replication origin. Examples of such expression vectors include pSV2dhfr (Subramani, S. et al. (1981) Mol. Cell. Biol., 1, 854–864), which has the early promoter of SV40; pEF-BOS (Mizushima, S. and Nagata, S. (1990) Nucleic Acids Res., 18, 5322), which has the promoter of human elongation factor; and pCEP4 (Invitrogen), which has the cytomegalovirus promoter. Moreover, the pME18S-FL3 vector (GenBank Accession No. AB009864) and the pME18S vector (Mol Cell Biol. 8:466–472 (1988)) can be used for cultured cells and individual organisms, respectively.

Insertion of the DNA of the present invention into the vector can be accomplished by the conventional method of ligase reaction using restriction sites (Current protocols in Molecular Biology edit. Ausubel et al. (1987) Publish. John Wiley & Sons, Section 11.4–11.11).

Moreover, the present invention relates to transformants carrying a vector of the present invention. There is no special limitation as to the host cell into which the vector of the present invention is transfected, and various host cells are used according to the particular purpose. Cells of eukaryote, such as vertebrate, insects, or yeasts can be used as the host cell for the overexpression of proteins. Specifically, simian COS cells (Gluzman, Y. (1981) Cell, 23, 175–182), Chinese hamster ovary (CHO) cells deficient in dihydrofolate reductase (Urlaub, G. and Chasin, L. A. (1980) Proc. Natl. Acad. Sci. USA, 77, 4216–4220), human embryonic kidney derived HEK293 cells, and 293-EBNA cells (Invitrogen), the EBNA-1 gene of Epstein Barr Virus transfected into the HEK293 cells, are well-known.

For example, when using COS cells as host cells, an expression vector having the SV40 replication origin to autonomously replicate in COS cells, as well as a transcription promoter, a transcription termination signal, and an RNA splice site can be used. Namely, vectors such as pME18S (Maruyama, K. and Takebe, Y. (1990) Med. Immunol., 20, 27–32), PEF-BOS (Mizushima, S. and Nagata, S. (1990) Nucleic Acids Res., 18, 5322), and pCDM8 (Seed, B. (1987) Nature, 329, 840–842) can be exemplified. The expression vector can be transfected into COS cells by method such as the DEAE-dextran method (Luthman, R. and Magnusson, G. (1983) Nucleic Acids Res., 11, 1295–1308), the calcium phosphate-DNA co-precipitation method (Graham, F. L. and van der Ed, A. J. (1973) Virology, 52, 456–457), the method using FuGENE6 (Boeringer Mannheim), and electroporation (Neumann, E. et al. (1982) EMBO J., 1, 841–845), and thus, desired transformed cells can be obtained.

Moreover, when using CHO cells as host cells, a vector which is capable of expressing the neo gene functioning as a G418 resistant marker, such as pRSVneo (Sambrook, J. et al. (1989): "Molecular Cloning-A Laboratory Manual" Cold Spring Harbor Laboratory, NY) or pSV2-neo (Southern, P. J. and Berg, P. (1982) J. Mol. Appl. Genet., 1, 327–341) may be co-transfected with the expression vector. Thus, by selecting G418 resistant colonies, transformed cells stably producing $LTC_4$ receptors can be obtained. Alternatively, in case of using 293-EBNA cells as host cells, target transformed cells can be obtained by using an expression vector such as pCEP4 (Invitrogen), having the replication origin of Epstein Barr Virus that is able to autonomously replicate in the 293-EBNA cells.

Preferably, the transformed cells of the present invention express the $LTC_4$ receptor on the cell membrane in a biologically active form. Therefore, when $LTC_4$ is made to act on these transformed cells, the response to the stimulation of $LTC_4$ is observed in the transformed cells. Such transformed cells can be used in the screening for compounds that modulate the binding activity of the $LTC_4$ receptor, as described below.

The transformant of the present invention can be cultured according to any conventional method, and the $LTC_4$ receptor of the present invention can be produced intracellularly or on the cell surface by the culture. As a medium to be used in the culture, various commonly used media can be properly selected according to the host cells employed. For example, in the case of COS cells, medium such as RPMI-1640 medium or Dulbecco's modified Eagle's minimal essential medium (DMEM) can be used, and, in case of necessity, supplemented with serum component such as fetal bovine serum (FBS). Moreover, in case of 293-EBNA cells, medium such as Dulbecco's modified Eagle's minimal essential medium (DMEM) supplemented with serum component such as fetal bovine serum (FBS) can be used by adding G418.

The $LTC_4$ receptor of the present invention, produced intracellularly or on the surface of the transformant by culturing the cells, can be separated and purified by various known separation methods. The separation and purification may be conducted as follows: for instance, after the membrane fraction containing $LTC_4$ receptor proteins has been solubilized, any of the following may be performed —treatment with ordinary protein precipitant; ultrafiltration; various liquid chromatography, such as molecular sieve chromatography (gel filtration), adsorption chromatography, ion-exchange chromatography, affinity chromatography, high-performance liquid chromatography (HPLC), and the like; dialysis; or a combination thereof. The membrane fraction can be obtained according to any conventional method. For instance, cells expressing $LTC_4$ receptors of the present invention on the surface can be cultured, and, after suspending them in the buffer, the desired membrane fraction can be obtained by homogenization and centrifugation. Moreover, by solubilizing the $LTC_4$ receptors using a solubilizing agent as mild as possible (CHAPS, Triton X-100, digitonin, etc.), the characteristic of receptors can be held even after solubilization.

The expression of the $LTC_4$ receptor of the present invention as a fusion protein, with marker sequences in frame, enables confirmation of the expression of the $LTC_4$ receptors and its intracellular localization, as well as purification of them, and such. Example of the marker sequences includes the FLAG epitope, Hexa-Histidine tag, Hemagglutinin tag, and myc epitope, and the like. Moreover, by inserting specific sequences recognized by proteases, such as enterokinase, factor Xa, and thrombin, between the marker sequence and the $LTC_4$ receptor, the marker sequence can be removed by those proteases. For instance, there is a report in which the muscarinic acetylcholine receptor and Hexa-Histidine tag are connected by the thrombin recognition sequence (Hayashi, M. K. and Haga, T. (1996) J. Biochem., 120, 1232–1238).

The present invention further relates to DNAs which hybridize specifically with the DNA consisting of the nucleotide sequences described in SEQ ID NO: 1 and have a strand length of at least 15 nucleotides. The phrase "hybridize specifically" with the DNA of the present invention indicates that the DNA hybridizes with the DNA of the present invention and does not hybridize with other DNAs under the ordinary hybridization condition, preferably under a stringent condition. Such DNAs can be used as probes, to detect and isolate the DNA of the present invention, and as primers, for amplification of the DNA of the present invention. DNAs used as primers generally have a chain length of 15 bp to 100 bp, preferably 15 bp to 40 bp. SEQ ID NO: 7 (forward primer) and SEQ ID NO: 8 (reverse primer) are indicated as preferable nucleotide sequences for the primer. Likewise, DNAs used as probes preferably have at least a part or the full sequence of the DNA of the present invention (or its complementary sequence) and have a chain length of at least 15 bp.

Probes and primers of the present invention can be used to detect variants of the $LTC_4$ receptor gene which relate to dysfunction. Deletion mutations and insertion mutations can be detected by the change in the size of the amplified product compared with that of a normal genotype. Point mutations can be identified by hybridizing the amplified DNA with labeled $LTC_4$ receptor nucleotides. It is known that completely matched and mismatched double strands are distinguished by RNase digestion or by a difference in melting temperature. Moreover, differences in the DNA sequence can be detected by determining the nucleotide sequence of regions where the sequence should be compared. Alternatively, the differences may be detected by mobility shift of electrophoresis of the DNA fragment, with or without denaturing agent in the gel (Myers, R. M. et al. (1985) Science. 230, 1242–1246).

Sequence variations at specific sites can be recognized by the nuclease protection assay (for example, RNase and S1 protection), as well as by the chemical cleavage method (Cotton et al. (1985) Proc Natl. Acad. Sci. USA 85:4397–4401).

An array of oligonucleotide probes which contain the nucleotide sequence of the $LTC_4$ receptor or fragments thereof can be constructed based on the present invention. The array technique is known, and is used to analyze gene expressions, genetic linkages, and genetic variabilities (Chee, M. et al. (1996) Science, 274, 610–613).

In addition, a method of measuring an abnormal decrease or increase of the level of the $LTC_4$ receptor from the sample obtained from the subject can be used for the diagnosis of diseases or susceptibility for the diseases resulting from hypoexpression, overexpression, and changed expression of $LTC_4$ receptors. The decrease or increase in expression can be measured at the RNA level by any polynucleotide quantitation method known to one skilled in the art, for example, PCR, RT-PCR, RNase protection, Northern blotting, and other hybridization methods.

The sample for the diagnosis based on these DNAs can be obtained from cells of subjects, for instance, blood, urine, saliva, biopsy, or autopsy specimens of tissue specimens.

Moreover, "a DNA which hybridizes specifically with the DNA described in SEQ ID NO: 1, with a chain length of at least 15 nucleotides" includes antisense DNA, for inhibition of expression of the protein of the present invention. The antisense DNA has a chain length of at least 15 bp or more, preferably 100 bp or more, more preferably 500 bp or more, to provoke the antisense effect. Generally, it has a chain length of 3000 bp or less, preferably 2000 bp or less. Such antisense DNAs may be applied to gene therapy of diseases caused by abnormalities of the protein of the present invention (e.g. dysfunction or expression disorder) and such. The antisense DNA can be prepared, for instance, by the phosphorothioate method (Stein, 1988 Physicochemical properties of phosphorothioate oligodeoxynucleotides. Nucleic Acids Res 16, 3209–21 (1988)) based on the sequence information of the DNA encoding the protein of the present invention (e.g. the DNA described in SEQ ID NO: 1). By knocking out the $LTC_4$ receptor gene using an antisense DNA of the present invention, elucidation of diseases in which $LTC_4$ receptor is involved can proceed.

For gene therapy, DNA or antisense DNA of the present invention can be administered to patients by ex vivo or in vivo method and such, using virus vectors such as retrovirus vector, adenovirus vector, and adeno-associated virus vector, nonviral vector such as liposome, and the like.

The present invention further relates to antibodies which bind to the proteins of the present invention. There is no limitation in the form of the antibody of the present invention, and polyclonal antibodies, monoclonal antibodies, or parts thereof having the antigen binding capacity are included. Moreover, antibodies of all classes are included. In addition, special antibodies, like humanized antibodies and such, are considered to be antibodies of the present invention.

Antibodies that react with the $LTC_4$ receptor of the present invention, for instance polyclonal antibodies and monoclonal antibodies, can be obtained by directly administering the $LTC_4$ receptor or fragments thereof to various animals. Moreover, it can be also obtained by the DNA vaccine method (Raz, E. et al. (1994) Proc. Natl. Acad. Sci. USA, 91, 9519–9523; Donnelly, J. J. et al. (1996) J. Infect. Dis., 173, 314–320), using a plasmid into which a gene encoding $LTC_4$ receptor of the present invention has been cloned.

Polyclonal antibodies are produced from sera or eggs of an animal such as rabbit, rat, goat, and chicken, in which the animals are immunized and sensitized by $LTC_4$ receptor protein or fragments thereof emulsified in suitable adjuvant such as Freund's complete adjuvant by intraperitoneal, subcutaneous, intravenous administration. Polyclonal antibodies can be separated and purified from the sera or eggs according to conventional methods for protein isolation and purification. Examples of the separation and purification methods suitable for polyclonal antibodies include, for instance, centrifugal separation, dialysis, salting-out with ammonium sulfate, chromatographic technique using such as DEAE-cellulose, hydroxyapatite, protein A agarose, and the like.

Monoclonal antibodies can be easily produced by one skilled in the art, according to the cell fusion method of Kohler and Milstein (Kohler, G. and Milstein, C. (1975) Nature, 256, 495–497). Mice are immunized intraperitoneally, subcutaneously, or intravenously for several times at an interval of few weeks by repeatedly inoculating emulsions, in which the $LTC_4$ receptor of the present invention or fragments thereof are emulsified into suitable adjuvant such as the Freund's complete adjuvant. The spleen cells are taken out after the final immunization, and then fused with the myeloma cell to prepare the hybridoma.

As the myeloma cell for obtaining a hybridoma, myeloma cells having markers, such as deficiency in hypoxanthine guanine, phosphoribosyltransferase or thymidine kinase, for instance, the mouse myeloma cell line P3X63Ag8.U1 are preferred. Furthermore, polyethylene glycol may be used as a fusing agent. Moreover, as the media for preparation of hybridomas, conventionally used media such as the Eagle's minimal essential medium, Dulbecco's modified minimal essential medium, RPMI-1640 can be used by adding properly 10 to 30% fetal bovine serum. The fused strains are selected by the HAT selection method. The culture supernatant of the hybridoma is screened by well-known methods, such as the ELISA procedure and immunohistological staining method, to select the hybridoma clone secreting the target antibody. Moreover, the monoclonality of the selected hybridoma is guaranteed by repeating subcloning by the limiting dilution method. Antibodies at an amount which can be purified are produced by culturing the thus obtained hybridoma in the medium for 2 to 4 days, or in the peritoneal cavity of pristane-pretreated BALB/c strain mouse for 10 to 20 days. Alternatively, the hybridoma can be cultured in media, such as those described above.

Monoclonal antibodies produced in the ascites or culture supernatant can be isolated and purified by conventional protein isolation and purification methods. Examples include centrifugal separation, dialysis, salting-out with ammonium sulfate, chromatographic technique using such as DEAE-cellulose, hydroxyapatite, and protein A agarose. Alternatively, monoclonal antibodies, or antibody fragments comprising parts thereof, can be also produced by inserting the whole or parts of gene encoding the antibody to the expression vector, and transfecting it into E. coli, yeast, or animal cells.

Furthermore, an antibody of the present invention which reacts with the $LTC_4$ receptor can be also obtained in the form of single chain Fv or Fab, according to methods of Clackson et al. or Zebedee et al. (Clackson, T. et al. (1991) Nature, 352, 624–628; Zebedee, S. et al. (1992) Proc. Natl. Acad. Sci. USA, 89, 3175–3179). Moreover, human antibodies can be also obtained by immunizing transgenic mice in which the antibody genes of the mouse are substituted by the human antibody genes (Lonberg, N. et al. (1994) Nature, 368, 856–859). Additionally, humanized antibodies can be prepared by genetic recombination, using hypervariable region of monoclonal antibodies (Methods in Enzymology 203, 99–121(1991)).

Antibody fragments comprising active parts of the antibody, for example, F(ab')$_2$, Fab, Fab' or Fv, can be obtained by digesting polyclonal or monoclonal antibodies of the present invention with proteases such as pepsin and papain by conventional methods, and isolating and purifying the resultant by standard protein isolation and purification methods.

Antibodies binding to the proteins of the present invention may be used, for example, in the diagnosis of expression disorders and structural abnormalities of proteins of the present invention, in addition to purification of protein of the present invention. Specifically, the presence of abnormality in expression or structure can be tested and diagnosed through the detection of the protein of the present invention by methods such as Western blot, competitive binding assay, immunoprecipitation, and ELISA, in which test samples are prepared by extracting protein from tissues, blood, cells, and so on.

Moreover, antibodies that bind to the proteins of the present invention may be used as therapy of diseases which are related to the protein of the present invention. When the antibody is used for therapeutic purposes, the human antibodies or the humanized antibodies are desirable due to its low immunogenicity.

The present invention further relates to methods for detecting $LTC_4$ receptor activity of the test compound using the protein of the present invention, and also to methods of screening for compounds that modulate the $LTC_4$ receptor activity, based on the detection method. The detection method of the present invention includes the steps of, (1) contacting the protein of the present invention with a test compound, and (2) measuring changes of the $LTC_4$ receptor activity of the protein of the present invention, Moreover, using the detection method, the screening method of the present invention can be conducted by selecting substances that modulate or modify the $LTC_4$ receptor activity. The term "modifying the $LTC_4$ receptor activity" means that it transduces signals by its binding to the $LTC_4$ receptor, or inhibits signal transduction elicited by $LTC_4$ by competing with $LTC_4$.

According to the detection method of the present invention, the changes of $LTC_4$ receptor activity are determined by the measuring activity index corresponding to the physiological characteristic of the $LTC_4$ receptor protein used in the screening. The activity index is, for example, the binding activity with a ligand, or response to the stimulation elicited by the binding of the ligand. Specifically, methods for detection described as follows can be exemplified. Moreover, although any compound can be used as a test compound for the screening method of the present invention, the following are examples of compounds that can be used as a test compound.

Various known compounds registered in the chemical files,

Peptides, antibodies to $LTC_4$ receptors, compounds obtained by the combinatorial chemistry techniques (Terrett, N. K., et al. (1995) Tetrahedron, 51, 8135–8137)

random peptides prepared by applying the phage-display method (Felici, F., et al. (1991) J. Mol. Biol., 222, 301–310) and such, culture supernatant of microorganisms, natural component derived from plants and marine organisms origin, animal tissue extracts, and chemically or biologically modified compounds or peptides which are selected by the screening method of the present invention.

Subsequently, a typical screening method is specifically explained below.

(a) Screening Method Using the Ligand Binding Assay Method

Compounds which bind to the $LTC_4$ receptor of the present invention can be screened by the ligand binding assay method. First, cell membranes expressing the $LTC_4$ receptor protein or purified sample of $LTC_4$ receptor protein are prepared. Cell membranes expressing the $LTC_4$ receptor protein or purified sample of $LTC_4$ receptor protein are incubated together with the labeled ligand and test compound for a certain time in a buffer solution, wherein assay conditions such as buffer, ion, pH are optimized. For instance, $[^3H]LTC_4$ can be used as the labeled ligand. After the reaction, and after filtration by glass filter and such, and washing with adequate volume of buffer solution, the radioactivity remaining on the filter is measured by using a liquid scintillation counter, for example. A compound which binds the $LTC_4$ receptor can be screened, using as an index the inhibition of specific binding of the labeled ligand under the existence of test compound.

For instance, a substance which shows an IC50 of 10 μM or less, more preferably 1 μM or less, can be selected under the ligand binding-assay condition described in Example 4, in which test compounds are incubated for a certain time with $[^3H]LTC_4$.

(b) Screening Method Using GTPγS Binding Method

Compounds which modify the activity of $LTC_4$ receptor of the present invention can be screened by the GTPγS binding method (Lazareno, S. and Birdsall, N. J. M. (1993) Br. J. Pharmacol. 109, 1120–1127). Cell membranes expressing the $LTC_4$ receptors are mixed with 400 pM of $^{35}S$ labeled GTPγS in a solution of 20 mM HEPES (pH 7.4), 100 mM NaCl, 10 M $MgCl_2$, and 50 mM GDP. After incubating with or without the test compound, the resultant is filtered by such as glass filters, and the bound GTPγS radioactivity is measured by using a liquid scintillation counter, and so on. Compounds which have agonistic activity to the $LTC_4$ receptor can be screened, using as an index the increase of specific GTPγS binding in the presence of the test compound. Moreover, compounds which have an antagonistic activity to the $LTC_4$ receptor can be screened by using the inhibition of the increase of GTPγS binding by $LTC_4$ or $LTD_4$ under the existence of the test compound as an index.

(c) Screening Method Utilizing the Changes of Intracellular $Ca^{++}$ and cAMP Concentration Compounds which modify the $LTC_4$ receptor activity of the present invention can be screened by utilizing the changes of intracellular $Ca^{++}$ or cAMP concentration in cells expressing the $LTC_4$ receptor. The measurement of $Ca^{++}$ concentrations can be accomplished by using fura2, fluo3, and such, and that of cAMP concentration can be accomplished by using a commercially available cAMP measuring kit (Amersham, etc.). Alternatively, by detecting the transcriptional activity of genes, wherein the level of transcription is regulated depending on the $Ca^{++}$ and cAMP concentrations, $Ca^{++}$ and cAMP concentrations can be indirectly measured. The $Ca^{++}$ and cAMP concentrations are directly or indirectly measured by exposing the test compound for a certain time to cells expressing the $LTC_4$ receptor and control cells which do not express the $LTC_4$ receptor. Compounds with agonistic activity can be screened, using as an index the increase of $Ca^{++}$ and/or the increase or decrease of cAMP concentration specific to cells expressing $LTC_4$ receptors compared with control cells. Moreover, compounds with antagonistic activity to the $LTC_4$ receptor can be screened, using as an index the inhibitory effect on the increase or decrease of $Ca^{++}$ and/or the increase or decrease of cAMP concentration by $LTC_4$ or $LTD_4$ under the existence of the test compound.

Compounds with antagonistic activity, which should be selected in the screening method of the present invention, can be defined as compounds competing with $LTC_4$ or $LTD_4$ against the $LTC_4$ receptor of the present invention, and not transducing any signals upon binding to the $LTC_4$ receptor. Although the affinity of antagonists for the $LTC_4$ receptor of the present invention is not limited, compounds with an IC50 of 10 μM or less, especially 1 μM or less are desirable. As used herein, the term antagonist is used as a synonymous term with blocking agent.

For instance, under the condition described in Example 5, substances with an IC50 of 10 μM or less, more preferably 1 μM or less, can be selected as substances with antagonistic activity, in which inhibitory effect of the test compound on the increase of intracellular $Ca^{++}$ stimulated by $LTC_4$ or $LTD_4$ after acting the test compound on cells for a certain time is used as an index.

Pharmaceuticals can be obtained using compounds, isolated by the screening methods described above, that modulate or modify the activity of $LTC_4$ receptor protein, as the main component and which target is the $LTC_4$ receptor. For instance, Compound A (N-(3,4-dimethyl-5-isoxazolyl)-6-(1-propyl-1H-benzimidazol-2-yl) -1-naphthalenesulfonamide) described in the Examples is an antagonist of $LTC_4$ receptor protein of the present invention with an IC50 of 1.2 μM. Compound A inhibits the binding of $LTC_4$ to $LTC_4$ receptor in a dose-dependent manner. In addition, compound A inhibits dose-dependently the cell migration activity of the $LTC_4$ receptor protein of the present invention and the response of coronary arterial smooth muscle cell by $LTC_4$. From these facts, it is clear that antagonists of the $LTC_4$ receptor protein of the present invention can be identified by the screening method of the present invention. Antagonists of the $LTC_4$ receptor protein of the present invention are useful as pharmaceuticals that target the $LTC_4$ receptor.

The pharmaceutical preparations containing the compound that modulate the activity of the $LTC_4$ receptor protein of the present invention as the active ingredient can be prepared, according to the type of the active ingredient, using a carrier, vehicle, and other additive normally used for pharmaceutical preparation. Administration methods, like oral administration of tablets, pills, capsules, granules, fine granules, powder, liquid medicine for oral administration, and such, as well as parenteral administration of injection agents such as intravenous injection and intramuscular injection, suppositories, transdermal administration agents, transmucosal administration agents, and so on can be mentioned. In particular, parenteral administration, such as intravenous injection, is preferable for peptides that tend to be digested in the stomach.

For the production of solid compositions for oral administration of the present invention, one or more active substances are mixed with at least one of the inactive diluents, such as lactose, mannitol, glucose, microcrystalline cellulose, hydroxypropylcellulose, starch, polyvinylpyrrolidone, and magnesium aluminometasilicate. The composition may contain inactive additive other than diluents, for example, lubricants, disintegrators, stabilizing agents, solubilizing agents, solubilizers, and such according to the conventional method. Tablets and pills may be coated with sugar or films of intestine-soluble substances or stomach-soluble substances, if necessary.

Liquid compositions for oral administration include emulsions, liquid agents, suspensions, syrups, and elixirs, and also generally used inert diluents such as purified water and ethanol. The composition may contain additive other than inert diluents, such as humectants, suspensions, sweeteners, flavoring agents, and preservatives.

Parenteral injections include aqueous and non-aqueous sterile liquid agents, suspensions, and emulsions. Water-soluble liquid agents and suspensions include, for example, distilled water for injection, physiological saline, and such as the diluent. Diluents for water insoluble liquid agents and suspensions include propylene glycol, polyethylene glycol, vegetable oil such as olive oil, alcohols such as ethanol, polysorbate 80, and so on. The composition may also contain such substances as humectant, emulsifying agent, dispersing agent, stabilizing agent, solubilizing agent or solubilizer, preservative, and so on. The composition is sterilized, for instance, by filtration through a bacteria reservation filter, mixing of a sterilizer, or irradiation. Alternatively, sterile solid compositions can be produced, and dissolved in sterile injection media such as sterile water before usage. The dosage of the drug of the present invention is properly determined in consideration of the activity of the active ingredient selected by the screening method described above, symptom, age and sex of the subject to be administered, etc.

For instance, in the case of oral administration, the usual dosage for adult (60 kg in weight) is about 0.1 to 100 mg, preferably 0.1 to 50 mg per day. Moreover, that for parenteral administration, 0.01 to 50 mg per day, preferably 0.01 to 10 mg per day in the form of injection.

BRIEF DESCRIPTION OF THE DRAWINGS

FIG. 8 shows the result of the dose-dependent inhibition of compound A to the increase of intracellular $Ca^{++}$ concentration in the coronary arterial smooth muscle cells by $LTC_4$. According to the figure, the vertical axis shows the fluorescence intensity, and the horizontal axis shows the time. Arrows indicate the experimental condition of each sequence.

BEST MODE FOR CARRYING OUT THE INVENTION

Figure 1:
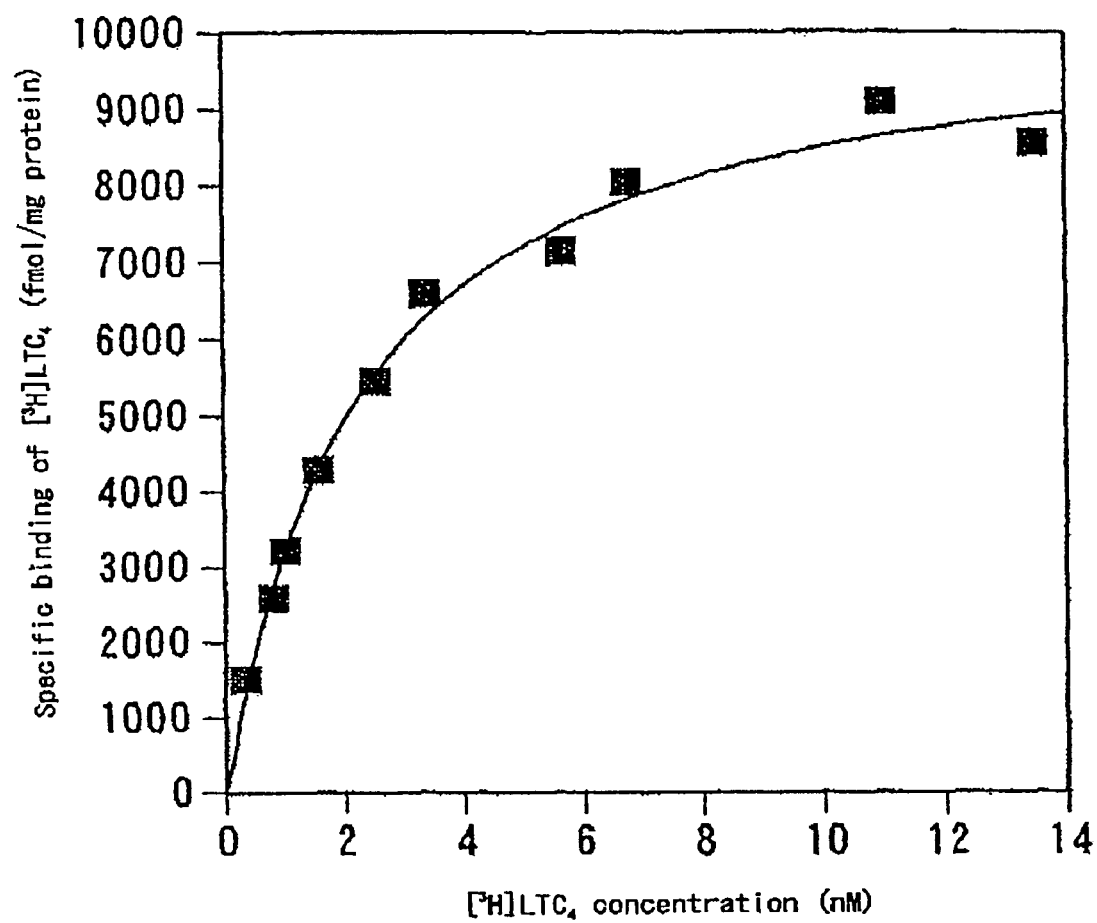
FIG. 1 is a graph showing the saturation curve of the specific binding of $[^3H]$-$LTC_4$ to the $LTC_4$ receptor. According to the figure, the vertical axis shows the amount of bound $[^3H]$-$LTC_4$ (fmol) per 1 mg protein, and the horizontal axis shows the $[^3H]$-$LTC_4$ concentration (nM) in the reaction solution.

The present invention is explained more specifically by following examples, but the present invention is not limited thereto.

EXAMPLE 1

Construction of the cDNA Library by the Oligo Cap Method

Total RNA was extracted from human placenta tissue (PLACE1), by the method described in the literature (J. Sambrook, E. F. Fritsch & T. Maniatis, Molecular Cloning Second edition, Cold Spring harbor Laboratory Press, 1989). Then, poly(A)+RNA was purified with oligo dT cellulose.

The cDNA library was made from poly(A)+RNA according to the oligo cap method (M. Maruyama and S. Sugano, Gene, 138:171–174 (1994)). According to the description in the literature (Suzuki and Sugano, Tanpakusitu Kakusan Koso, 41: 197–201 (1996), Y. Suzuki et al., Gene, 200: 149–156 (1997)), using oligo-cap linker (SEQ ID NO: 3) and oligo dT primer (SEQ ID NO: 4), BAP (Bacterial Alkaline Phosphatase) treatment, TAP (Tobacco Acid Phosphatase) treatment, RNA ligation, first-strand cDNA synthesis, and removal of the RNA were accomplished. Then, the resultant was converted into a double-strand cDNA by PCR (polymerase chain reaction), using PCR primers of 5' (SEQ ID NO: 5) and 3' (SEQ ID NO: 6), and digested with SfiI. Thereafter, the resultant was directionally ligated into pME18SFL3 vector (GenBank AB009864, Expression vector) digested with DraIII, to construct the cDNA library. Clones with inserted cDNA size of 1 kb or less were excluded from clones of the cDNA library. Then, nucleotide sequences of 5' end and 3' end of cDNA were analyzed by DNA sequencer (ABI PRISM 377, PE Biosystems) after sequencing reaction according to the manual, using DNA sequencing reagent (Dye Terminator Cycle Sequencing FS Ready Reaction Kit, dRhodamine Terminator Cycle Sequencing FS Ready Reaction Kit or BigDye Terminator Cycle Sequencing FS Ready Reaction Kit, PE Biosystems).

EXAMPLE 2

Selection of Clones Having a Signal Sequence

As for deduced amino acid sequence predicted from all ATG codon in the 5'-terminal sequence, clones predicted to have a signal sequence were selected specifically, by analyzing the presence of sequence predicted to be the signal peptide characteristic to amino terminus of many secretory proteins using the protein localization predicting program "PSORT" developed by Nakai and Kanehisa. By this selection, clones with high possibility to encode secretory proteins or membrane proteins were chosen. From the data of 5'-end sequence data (one pass sequencing), clones with maximum ATGpr1 (A. A. Salamov, T. Nishikawa, M. B. Swindells, Bioinformatics, 14: 384–390 (1998); http://www.hri.co.jp/atgpr/) of 0.7 or more, having signal sequence (analyzed by PSORT) and at the same time ORF in the 5' end sequence data were selected.

EXAMPLE 3

Sequencing of PSEC0146

As for clones selected by Example 2, the nucleotide sequence of the full-length cDNA, and deduced amino acid sequence were determined. Final nucleotide sequences were determined by combining the three methods described below, namely by perfectly overlapping the nucleotide sequences determined by each method. The deduced amino acid sequence was revealed from the determined cDNA sequence.

(1) Long-read sequencing from both ends of the cDNA-inserted fragment using Licor DNA sequencer (the DNA nucleotide sequences were analyzed by Licor sequencer after sequencing reaction according to the manual of Licor sequencer (Aloka));

(2) nested sequencing by Primer Island method using in vitro transposition of AT2 transposon (S. E. Devine and J. D. Boeke, Nucleic Acids Res., 22: 3765–3772, (1994)) (Clones were obtained using the kit of PE Biosystems according to the manual, and then the sequence reaction was carried out using the DNA sequencing reagent of PE Biosystems according to the manual, and the DNA nucleotide sequences were analyzed using ABI PRISM 377); and (3) primer walking by the dideoxy-terminator method using custom synthetic DNA primers (sequence reaction was carried out using custom synthetic DNA primers and the DNA sequencing reagent of PE Biosystems according to the manual, and then, the DNA nucleotide sequence was analyzed by ABI PRISM 377).

Analysis by ATGpr and PSORT as well as BLAST analysis in GenBank and SwissProt was carried out for the obtained sequences. Most clones were presumed to be secretory proteins or membrane proteins with signal sequence at its N-terminus. One of thus determined full-length cDNA was named PSEC0146. The nucleotide sequence of PSEC0146 is described in SEQ ID NO: 1 and the deduced amino acid sequence encoded by the nucleotide sequence is described in SEQ ID NO: 2.

EXAMPLE 4

Expression of $LTC_4$ Receptor in COS Cells and Binding Experiment with $LTC_4$

The $LTC_4$ receptor activity of the protein encoded by PSEC0146 was confirmed by experiments described below. First, to express the protein encoded by the cDNA, the cDNA was obtained by RT-PCR using poly(A)+ RNA of human spleen (Clontech) as the template. The nucleotide sequence of the primer necessary for RT-PCR was designed based on the nucleotide sequence information determined in Example 3.

Oligonucleotides described in SEQ ID NO: 7 and described in SEQ ID NO: 8, in which the XbaI site was added to the 5' end of each oligonucleotide, were used as the forward primer and a reverse primer, respectively, for RT-PCR. RT-PCR was carried out using Pyrobest DNA polymerase (Takara Shuzo) with 34 reaction cycles of 98° C. (10 sec)/58° C. (30 sec)/72° C. (2 min) under the existence of 5% DMSO. As a result, a DNA fragment of about 1.0 kbp was amplified. After digesting this fragment with XbaI, the resultant was cloned into pEF-BOS plasmid (Mizushima, S. and Nagata, S. (1990) Nucleic Acids Res., 18, 5322). The nucleotide sequences of obtained clones were analyzed by the dideoxy-terminator method using ABI377 DNA Sequencer (Applied Biosystems). The plasmid obtained was confirmed to have the sequence encoding the full-length of the amino acid sequence described in SEQ ID NO: 2. The plasmid was designated as pEF-BOS-PSEC0146.

Figure 2:
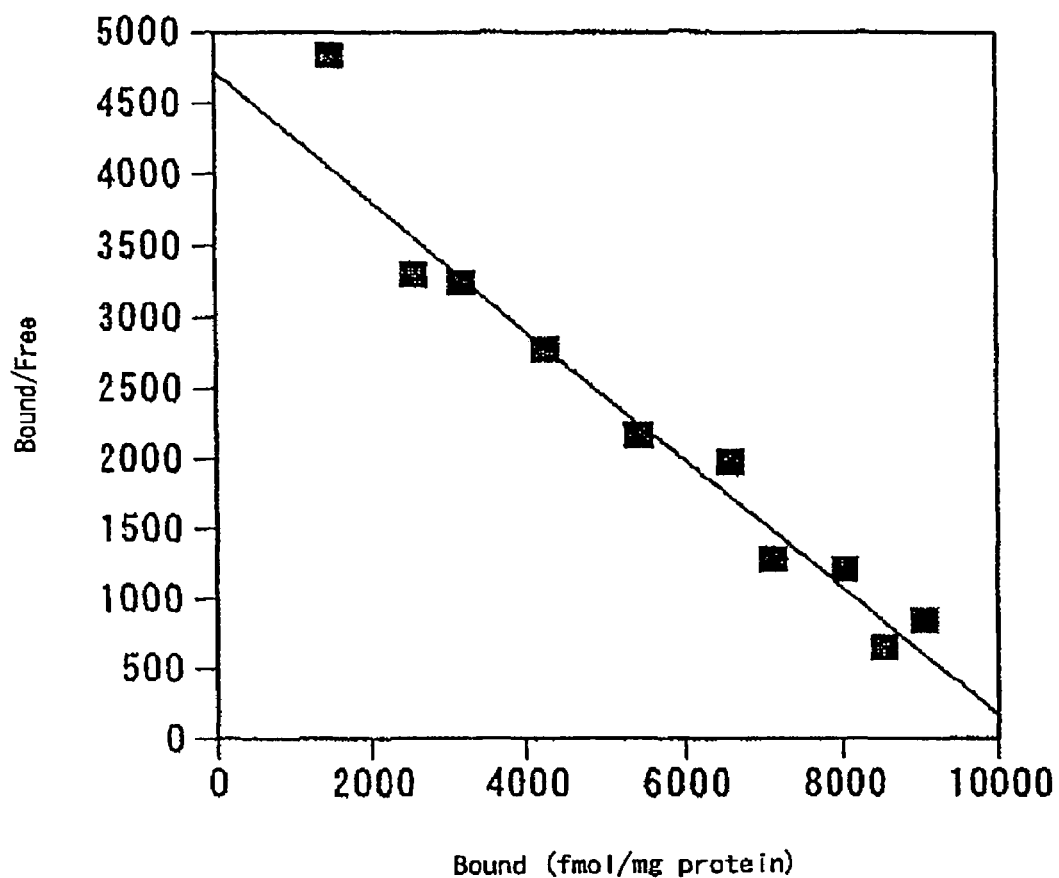
FIG. 2 shows the result of the Scatchard analysis of the specific binding of $[^3H]$-$LTC_4$ to the $LTC_4$ receptor. According to the figure, the vertical axis shows the binding ratio (bound/free ratio), and the horizontal axis shows the amount of bound $(^3H)$-$LTC_4$ (fmol) per 1 mg protein.

$2 \times 10^6$ COS-1 cells were inoculated to a 175 mm2 culture flask and cultured for 36 hours, and then, 50 μg of pEF-BOS-PSEC0146 or pEF-BOS (empty vector) was transfected using FuGENE6 (Boeringer Mannheim) Cells cultured for 36 hours following gene transfection were recovered and washed, then suspended in 20 mM Tris-HCl (pH 7.4), 5 mM EDTA and homogenized with a Polytron homogenizer. After ultracentrifugation, the homogenized cells were suspended in 50 mM HEPES (pH 7.4), 40 mM $MgCl_2$, 1 mM EGTA as a membrane fraction. 0.5 to $14 \times 10^{-9}$ M of [$^3$H]-$LTC_4$ (Daiichi Pure Chemicals) at final concentration was added to 5 μg of the membrane fraction, and incubated 1 hour at room temperature in 250 μl solution comprising 50 mM HEPES (pH 7.4), 40 mM $MgCl_2$, 1 mM EGTA, 5 mM L-Serine, 10 mM Borate, 2 mM L-Cystein, and 2 mM L-Glycine. Thereafter, the membrane fraction was recovered on a glass filter using a cell harvester. Micro-scintillator was added to the glass filter and the total binding to the membrane fraction was measured by using a liquid scintillation counter. Further, by adding $LTC_4$ (CAYMAN) at a final concentration of 2 μM to the assay described above, non-specific binding to the membrane fraction was measured. As a result, it was clarified that [$^3$H]-$LTC_4$ binds specifically to membrane fractions of COS-1 cells into which pEF-BOS-PSEC0146 were transfected. FIG. 1 shows the saturation curve of the specific binding of [$^3$H]-$LTC_4$ to membrane fraction of COS-1 cells into which pEF-BOS-PSEC0146 were transfected. Moreover, the result of Scatchard analysis on this binding is shown in FIG. 2. The result of Scatchard analysis showed that the dissociation constant of $LTC_4$ binding to the membrane fraction of COS-1 cells into which pEF-BOS-PSEC0146 were transfected is Kd=2.20 nM and that the maximum binding is Bmax=10.4 pmol/mg protein. On the other hand, no specific binding was observed for the membrane fraction of COS-1 cells into which empty vectors were transfected.

As mentioned above, the $LTC_4$ receptor of the present invention was confirmed to be a receptor with a high affinity to $LTC_4$, the entity of which has been unknown though the existence of which had been suggested. Binding experiments and screening of ligands became possible for the first time by using cells transformed with the present $LTC_4$ receptor.

EXAMPLE 5

Figure 3:
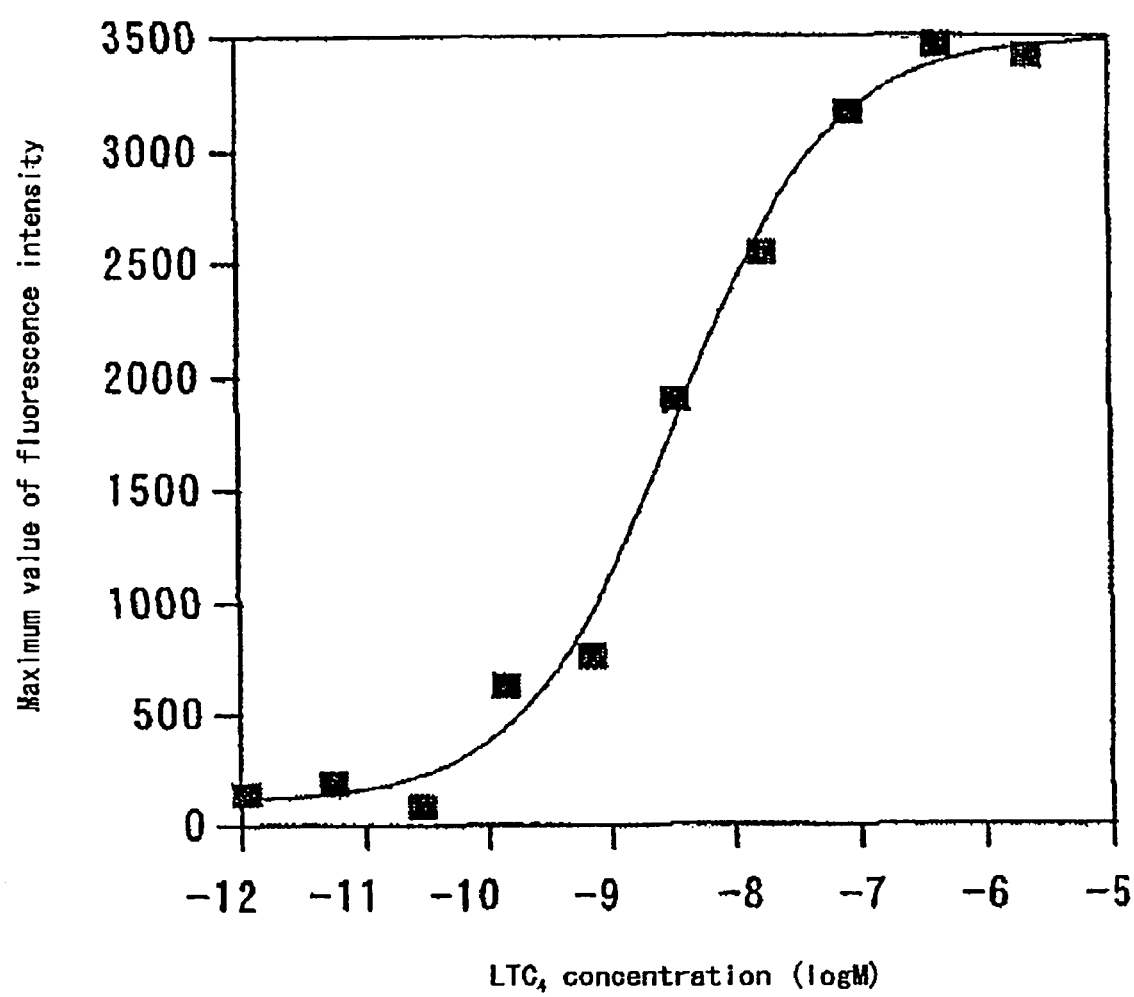
FIG. 3 shows the result of the dose dependency of $LTC_4$ to the increase of intracellular $Ca^{++}$ concentration. According to the figure, the vertical axis shows the maximum value of fluorescence intensity (counts), and the horizontal axis shows the $LTC_4$ concentration in reaction solution (logM).

Expression of $LTC_4$ Receptor in HEK293-EBNA Cells and Changes in Intracellular $Ca^{++}$ Concentration by $LTC_4$ $2.5 \times 10^4$ cells per well of HEK293-EBNA cells were inoculated to 96 well Black/clear bottom plate, collagen type I coated (BECTON DICKINSON). After culturing for 24 hours, 40 ng per well of pEF-BOS-PSECO 146 or pEF-BOS (empty vector) were transfected into the cells using FuGENE6 (Boeringer Mannheim). 24 hours after gene transfection, the medium was discarded, 100 μl per well of DMEM containing 4 μM Fluo-3, AM (Molecular Probe), 0.004% pluronic acid, and 10% FBS was added and incubated for 1 hour at 37° C. Following incubation, cells were washed four times with Hanks BSS containing 20 mM HEPES (GIBCO), then 100 μl per well of Hanks BSS containing 20 mM HEPES was added. The time course of the changes of intracellular $Ca^{++}$ concentration was measured using FLIPR (Molecular Device). Namely, 10 seconds after the start of the measurement, $LTC_4$ was added at a final concentration of $2 \times 10^{-6}$ M to $1 \times 10^{-12}$ M, and fluorescence intensity was measured every 1 second for the first 50 seconds and further every 6 seconds for the following 4 minutes. A $LTC_4$ dose dependent increase of intracellular $Ca^{++}$ concentration was observed in cells into which pEF-BOS-PSEC0146 had been transfected. On the other hand, no changes in intracellular $Ca^{++}$ concentration were observed in cells into which empty vectors had been transfected. Results are shown in FIG. 3. According to FIG. 3, the maximum fluorescence intensity of the data of changes of intracellular $Ca^{++}$ concentration in cells, into which pEF-BOS-PSEC0146 had been transfected, is plotted on the vertical axis, and the $LTC_4$ concentration is plotted on the horizontal axis. The $LTC_4$ dose-dependence of intracellular $Ca^{++}$ changes in cells, into which pEF-BOS-PSEC0146 had been transfected, was analyzed by Logistic regression. As a result, it was revealed that the EC50 of $LTC_4$ was 3.46 nM. Further, the result obtained by a similar analysis of $LTD_4$ dose-dependence of intracellular $Ca^{++}$ changes by Logistic regression revealed that the EC50 of $LTD_4$ was 3.68 nM. As described above, it was confirmed that cells, into which the $LTC_4$ receptor of the present invention had been transfected, induce changes of intracellular $Ca^{++}$ concentration in a dose-dependent manner in response to $LTC_4$ and $LTD_4$. By measuring the changes of intracellular $Ca^{++}$ concentration, the activity of the test compound to modulate the $LTC_4$ receptor activity can be detected. Further, by selecting compounds which increase or decrease the $LTC_4$ receptor activity based on the detection method, screening of agonists and antagonists became possible.

EXAMPLE 6

Construction of CHO Cells Stably Expressing $LTC_4$ Receptors pEF-BOS-dhfr-PSEC0146 was used as the expression vector to express human $LTC_4$ receptor. $1 \times 10^6$ cells of CHO-dhfr(-) cell was inoculated to a 10 cm culture dish using αMEM (with nucleic acid), and after culturing for a day, 8 μg of pEF-BOS-dhfr-PSEC0146 was transfected using FuGENE6 (Boeringer Mannheim). After 24 hours, gene transfected cells were recovered, and after suspending in αMEM (without nucleic acid)/100 nM Methotrexate (Wako), the suspension was serially diluted and seeded again onto 10 cm culture dishes. Colonies appeared after two weeks were obtained as CHO cells stably expressing $LTC_4$ receptors.

For the binding assay with $LTC_4$, after culturing CHO cells stably expressing $LTC_4$ receptors, cells were recovered and washed, then suspended in 20 mM Tris-HCl (pH 7.4), 5 mM EDTA and homogenized by using the Polytron homogenizer. Following ultracentrifugation, the resultant was suspended in 50 mM HEPES (pH 7.4), 40 mM $MgCl_2$, 1 mM EGTA to prepare the membrane fraction. The binding experiment of [$^3$H]-$LTC_4$ was carried out under the same condition as in Example 4 using 15 μg of the membrane fraction. The saturation curve of the specific binding of [$^3$H]-$LTC_4$ to the membrane fraction of the CHO cells stably expressing the $LTC_4$ receptors was plotted as in Example 5. Furthermore, the result of the Scatchard analysis of this binding assay revealed that the dissociation constant of $LTC_4$ binding to the membrane fraction of CHO cells stably expressing the $LTC_4$ receptors was Kd=2.65 nM, and the maximum binding was Bmax=6 pmol/mg protein.

Moreover, to measure the changes of intracellular $Ca^{++}$ concentration, $2 \times 10^4$ cells/well of CHO cells stably expressing $LTC_4$ receptor were inoculated to 96 well Black/clear bottom plate (BECTON DICKINSON). After culturing for 24 hours, medium was discarded and 100 μl/well of Hanks BSS containing 4 μM Fluo-3, AM (Molecular Probe), 0.004% pluronic acid, 1% FBS, 20 mM HEPES, and 2.5 mM probenecid was added, and incubated at 37° C. for 1 hour. The changes of intracellular $Ca^{++}$ concentration through $LTC_4$ and $LTD_4$ were measured by FLIPR under the same condition as in Example 5. The dose dependent changes of intracellular $Ca^{++}$ concentration of CHO cells stably expressing the fi $LTC_4$ receptors elicited by $LTC_4$ and $LTD_4$ were analyzed by the Logistic regression. As a result, it was revealed that the EC50 of $LTC_4$ was 0.44 nM and that of $LTD_4$ was 0.59 nM.

As described above, it was confirmed that $LTC_4$ receptor of the present invention in CHO cells stably expressing the $LTC_4$ receptors also shows high affinity to $LTC_4$ and that it induces a $LTC_4$ dose dependent increase of intracellular Ca$^{++}$ concentration as in COS cells or HEK293-EBNA cells that express the receptors transiently

EXAMPLE 7

Tissue Distribution of Human LTC$_4$ Receptor Gene Expression

The expression pattern of human LTC$_4$ receptor gene was analyzed by Northern blot hybridization. A cDNA fragment (nucleotide sequence from 947 to 1626 of SEQ ID NO: 1) was used as the probe for the human LTC$_4$ receptor gene. Hybridization of the probe and membrane (Clontech) blotted with poly(A)+ RNA (2 µg) derived from various human organs was carried out in a solution containing 50% formamide, 5×SSPE, 10× Denhardt's solution, 2% SDS, and 100 µg/ml denatured salmon sperm DNA at 42° C. for 22 hours. The membrane was finally washed twice with a solution containing 0.2× SSC, 0.1% SDS at 65° C. for 20 min.

Figure 4:
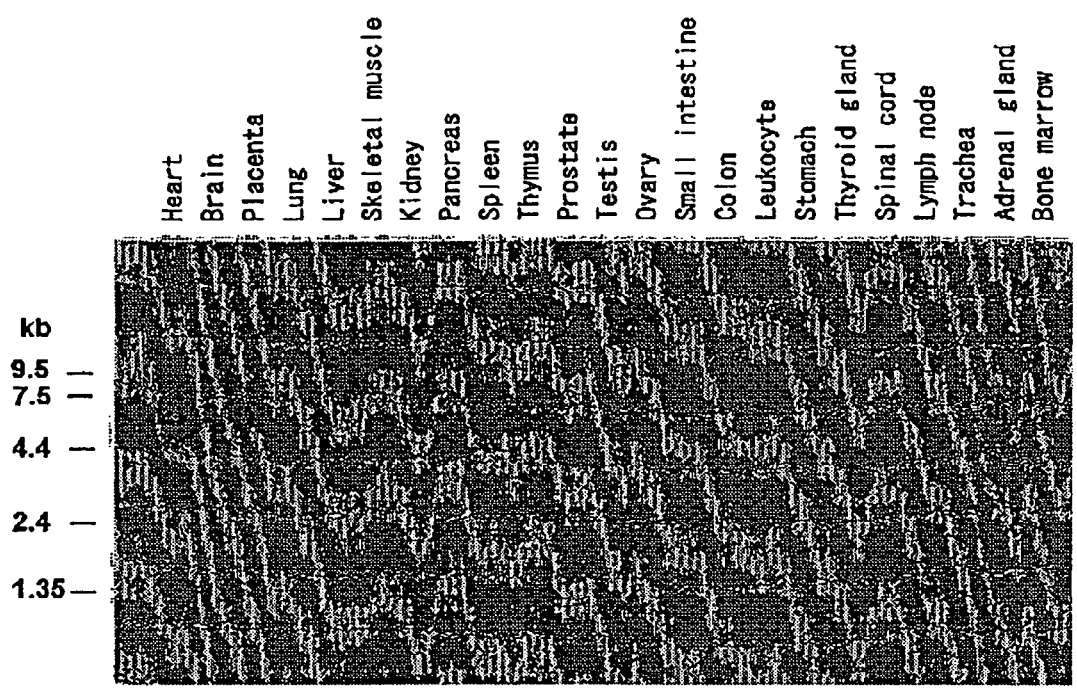
FIG. 4 is a photograph showing the result of analysis on the distribution of the gene expression of human $LTC_4$ receptor in the tissue by Northern blot hybridization.

According to the Northern blot analysis of human organs (heart, brain, placenta, lung, liver, skeletal muscle, kidney, pancreas, spleen, thymus, prostate, testis, ovary, small intestine, colon, peripheral blood leukocyte, stomach, thyroid gland, spinal cord, lymph node, trachea, adrenal gland, and born marrow), mRNA of approximately 5 kb was strongly detected in heart, placenta, spleen, peripheral blood leukocyte, and adrenal gland, as shown in FIG. 4. Although weak, signals were also observed in brain, kidney, prostate, ovary, spinal cord, and lymph node. Taken together, LTC$_4$ receptor of the present invention is expected to be involved in cardiovascular disturbance, inflammation, and allergic symptoms caused by peptide leukotrienes.

EXAMPLE 8

Distribution of Human LTC$_4$ Receptor Gene Expression in Cardiovascular System

The distribution of human LTC$_4$ receptor gene expression in cardiovascular system was analyzed by the PCR method.

Single strand cDNA derived from parts of human heart (left atrium, right atrium, left ventricle, right ventricle, artery, vein, intraventricular septum, and pericardium) (Bio-Chain) was used as the template, and the oligonucleotide in SEQ ID NO: 9 and the oligonucleotide in SEQ ID NO: 10 were used as the forward primer and the reverse primer, respectively, for the PCR, The PCR was carried out using Taq DNA polymerase (Takara Shuzo) under the existence of 5% DMSO, with 30 cycles of 94° C. (30 sec)/50° C. (30 sec)/72° C. (1 min). As the internal control, PCR with the same condition was carried out using cDNA of human parts described above as a template and Human G3PDH Control Amplimer Set (Clontech). The reaction product was analyzed by electrophoresis on a 1% agarose gel. Moreover, total PNA was purified from normal human coronary arterial endothelial cells, normal human coronary arterial smooth muscle cells, normal human lung microvascular endothelial cells, normal-human adult dermal microvascular endothelial cells, normal-human neonatal dermal microvascular endothelial cells, normal human aortic endothelial cells, normal human pulmonary artery endothelial cells, and normal human umbilical vein endothelial cells (Clonetics) using ISOGEN (Nippon Gene). 5 µg of the total RNA of derived from each cells were reacted with DNase (Nippon Gene) at 37° C. for 15 min. The total RNA treated with DNase was converted to cDNA with SuperScript First-strand System (for RT-PCR) (GIBCO). Using the cDNA as template, PCR was performed under the same condition as described above.

Figure 5:
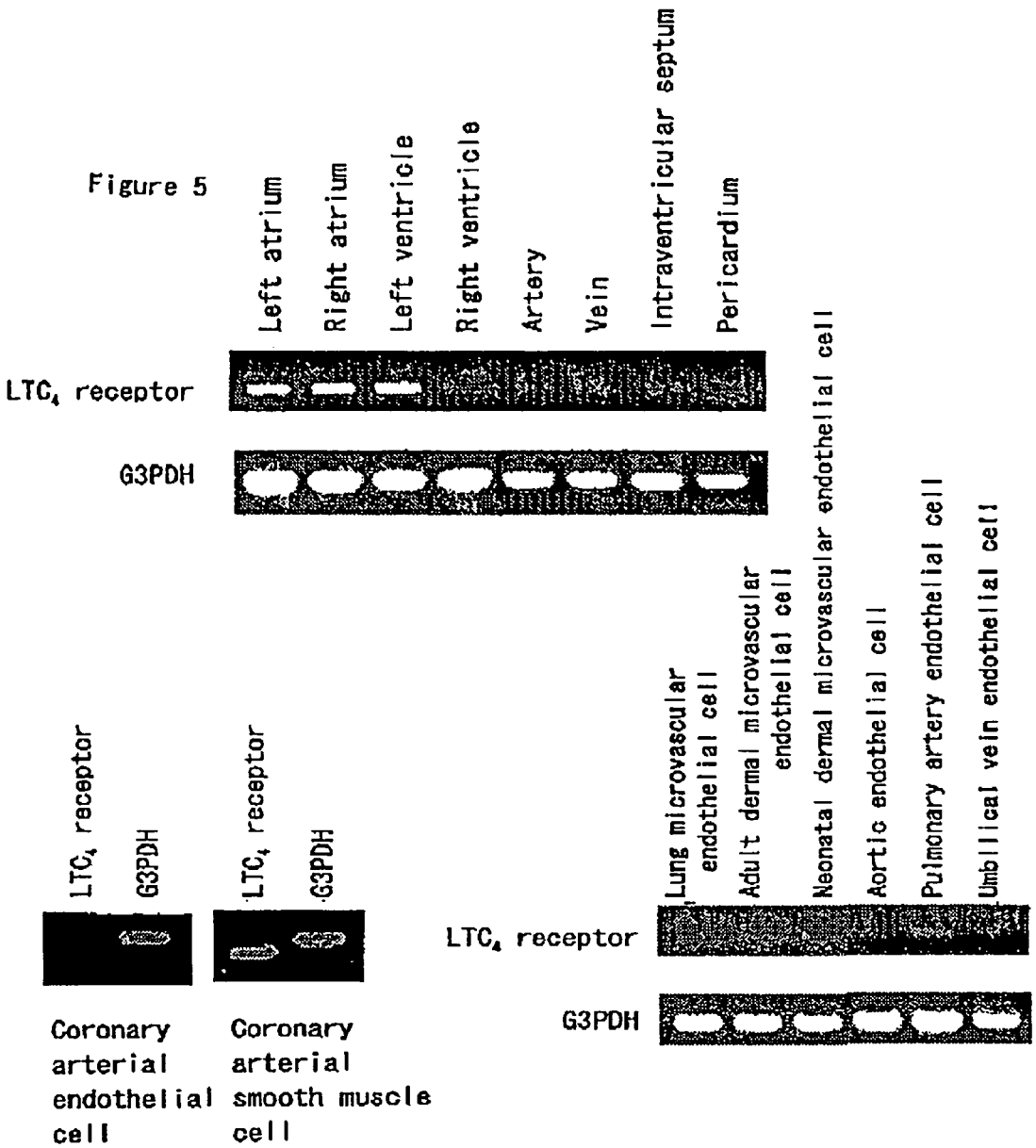
FIG. 5 is a photograph showing the result of analysis on the distribution of the gene expression of human $LTC_4$ receptor in the cardiovascular system by the PCR method.

The result is shown in FIG. 5. Amplification product of LTC$_4$ receptor with a length of about 450 bp was strongly detected in left atrium, right atrium, left ventricle, right ventricle, and coronary arterial smooth muscle cells. Moreover, although weak, signals were also detected in intraventricular septum, pericardium, lung microvascular endothelial cells, adult dermal microvascular endothelial cells, neonatal dermal microvascular endothelial cells, pulmonary artery endothelial cells, and umbilical vein endothelial cells. From the results described above, LTC$_4$ receptor of the present invention is expected to be involved in the process of the decrease in cardiac contractility and coronary flow, which are known to be led by the peptide leukotrienes.

EXAMPLE 9

Distribution of Gene Expression of Human LTC$_4$ Receptor in Blood Cells

Heparinized blood was collected from a healthy volunteer, and was left standing for 1 hour at room temperature following addition of 1/3 volume of 6% dextran/saline. The supernatant was taken and after 5 min centrifugation at 150×g, the pellet was suspended in Hunk's Balanced Salt Solution (HBSS). The resultant was loaded on equal volumes of Ficoll-Paque (Pharmacia) and centrifuged at 400×g for 30 min. The intermediate layer and the pellet were collected as the mononuclear cell fraction and the polynuclear leukocyte, respectively. CD16 microbeads (Daiichi Pure Chemicals) were added to polynuclear leukocytes and were separated into neutrophil fraction and eosinophil fraction by using a magnetic stand. Mononuclear cell fraction, neutrophil fraction, and eosinophil fraction were separately washed with saline and the total RNA were purified using ISOGEN (Nippon Gene). 5 µg total RNA derived from each fraction was reacted with DNase (Nippon Gene) at 37° C. for 15 min. Total RNA treated with DNase was converted to cDNA using SuperScript First-strand System (for RT-PCR) (GIBCO).

The distribution of LTC$_4$ receptor expression was analyzed by PCR using cDNA of blood cell fractions described above as the template under the same condition as in Example 8. The amplification product of about 450 bp of LTC$_4$ receptor was detected in each blood cell fraction of healthy human A and B. Especially, it could be detected well in eosinophils. From results described above, it was expected that LTC$_4$ receptor of the present invention is involved in diseases caused by eosinophils, for example, allergic disease such as asthma.

EXAMPLE 10

Mapping of the Human LTC$_4$ Receptor Gene

To determine the chromosomal position of the human LTC$_4$ receptor gene, PCR was performed using human/hamster radiation hybrid panel GeneBridge 4 panel (Sanger Center) and G3 panel (Stanford University) (Research Genetics) as the template, oligonucleotide shown in SEQ ID NO: 11 as the forward primer, and oligonucleotide shown in SEQ ID NO: 12 as the reverse primer. PCR was carried out using Pyrobest DNA polymerase (Takara Shuzo) under the existence of 5% DMSO, with 34 cycles of 98° C. (10 sec)/58° C. (30 sec)/72° C. (2 min). The presence of an amplification product of about 600 bp DNA fragment specific to the LTC$_4$ receptor for each vector included in the panel was judged as positive or the absence as negative, and the result was analyzed through the Internet at http://www- .genome.wi.mit.edu and http://www-shgc.stanford.edu/RH/index.html. As a result, the $LTC_4$ receptor gene of the present invention was located most closely to chromosomal markers, D13S153 (GeneBridge 4) and SHGC-12474 (G3), on chromosome 13q14. Linkage of this chromosomal location to atopic asthma has been reported (Kimura, K., et al. (1999) Human Molecular Genetics 8, 1487–1490). Moreover, in the chromosomal location, deletion of a gene is confirmed in B cell leukemia patients (Kalachikov, S., et al. (1997) Genomics 42, 369–377). The mutation in the present $LTC_4$ receptor gene was expected to be related to the above-mentioned diseases.

EXAMPLE 11

Screening of Compounds, which Inhibit Binding Between the $LTC_4$ Receptor and $LTC_4$, Using CHO Cells Stably Expressing $LTC_4$ Receptors Candidate compounds were screened, with the activity to inhibit the $LTC_4$ binding as an index, using the membrane fraction of CHO cells stably expressing $LTC_4$ receptor prepared in Example 6. Specifically, candidate compounds of constant concentration and $0.5 \times 10^{-9}$ M $[^3H]$-$LTC_4$ were added to the solution consisting of 50 mM HEPES (pH 7.4), 40 mM $MgCl_2$, 1 mM EGTA, 5 mM L-Serine, 10 mM Borate, 2 mM L-Cystein, and 2 mM L-Glycine, containing 15 μg of membrane fraction of CHO cells stably expressing $LTC_4$ receptors, and after incubating at room temperature for 1 hour, the resultant was recovered on the glass filter by a cell harvester. Micro-scintillator was added to the glass filter and the radioactivity was measured by a liquid scintillation counter. Simultaneously, radioactivities of that without the candidate compound and that with the addition of $LTC_4$ at a final concentration of 1 μM in the above-mentioned assay were measured as total binding amount and non-specific binding amount, respectively. For example, N-(3,4-dimethyl-5-isoxazolyl)-6-(1-propyl-1H-benzimidazol-2-yl)-1-naphthalenesulfonamide (compound A) can be exemplified as a compound with an IC50 of 10 μM or less, under this condition. The compound inhibited the binding of $LTC_4$ to $LTC_4$ receptor dose-dependently, with an IC50 of 1.2 μM. Compound A was produced as follows.

PRODUCTION EXAMPLE 1

Tetramethylsilane (δ; 0.00 ppm) was used as the internal standard for $^1H$ NMR.

PRODUCTION EXAMPLE 1-1

2-(2-naphthyl) benzimidazole 2.335 g phenylenediamine was added to 40 ml methylene chloride, 4.105 g of 2-naphthoyl chloride was further added and stirred overnight at room temperature. The solvent was evaporated to obtain 6.391 g of colorless solid.

40 ml 1,3-dimethyl-2-imidazolidinone was added to the solid with and stirred overnight at 170° C. The solvent was evaporated under vacuum, and after dissolving the residue to ether washed with saturated sodium bicarbonate solution and saturated brine solution. After dehydrating the ether layer on magnesium sulfate and evaporating solvent, about 6.5 g of brown solid was obtained. By separating and purifying the crude product using silica gel column chromatography (chloroform), 3.514 g (67%) of 2-(2-naphthyl) benzimidazole was obtained. GC MS; 244($M^+$)

PRODUCTION EXAMPLE 1-2

2-(2-naphthyl)-1-propyl benzimidazole 1.486 g of 2-(2-naphthyl)benzimidazole obtained in Production example 1-1 was dissolved in 20 ml N,N-dimethylformamide and 300 mg of 60% sodium hydride was added. After stirring for 15 min, 0.72 ml of propyl iodide was added and was further stirred for 1 hour. After evaporating the solvent under vacuum, 1N sodium hydroxide was added and extracted with ether. After dehydrating the ether layer on magnesium sulfate and evaporating the solvent, reddish residue was obtained. By separating and purifying the crude product using silica gel column chromatography (chloroform-hexane; 1:1 to chloroformalone) 1.195 g (77%) of colorless solid of 2-(2-naphthyl)-1-propyl benzimidazole was obtained.

$^1H$ NMR (90 MHz, $CDCl_3$); 0.85 (t, 3H), 1.74–1.99 (m, 2H), 4.18–4.35 (m, 2H), 7.25–8.21 (m, 11H) GC MS; 286 ($M^+$)

PRODUCTION EXAMPLE 1-3

N-(3,4-dimethyl-5-isoxazolyl)-6-(1-propylimidazol-2-yl)naphthale ne sulfonamide 1.601 g of 2-(2-naphthyl)-1-propyl benzimidazole obtained in Production example 1-2 was dissolved in 4 ml chloroform, and 1.2 ml chlorosulfuric acid and 2 ml chloroform solution were added drop wise at room temperature. Then, it was refluxed with heating for 2 hours, and after cooling the reaction mixture separated into the upper (chloroform) and lower (product) layers. After separating the upper layer, brown oil was obtained by washing the lower layer with chloroform.

3.2 ml propylamine and 2 ml chloroform was added to the compound and refluxed with heating for 5 min. After cooling, 10 ml phosphorus oxychloride was added and was further refluxed with heating for 30 min. After cooling, the reaction mixture was poured into ice-chilled water and extracted with chloroform. After washing the chloroform layer with saturated sodium bicarbonate solution and saturated brine solution, it was dehydrated on magnesium sulfate. The solvent was removed by evaporation under vacuum, and 2.703 g of crude product was obtained.

The methylene chloride solution (5 ml) of the product was added to a solution in which 457 mg of 5-amino-3,4-dimethyl isoxazole was dissolved in 2 ml pyridine. After stirring for 1 day, chloroform was added, and following washing with 0.1N hydrochloric acid and saturated brine solution, it was dehydrated on magnesium sulfate. After evaporating the solvent under vacuum, brown foam was obtained. It was separated using intermediate pressure silica gel column chromatography (chloroform-methanol; 100:1 to 10:1), and by recrystallizing the crude product with acetone-hexane-ether, 221 mg (12%) of N-(3,4-dimethyl-5-isoxazolyl)-6-(1-propylimidazol-2-yl)naphthale ne sulfonamide was obtained.

$^1H$ NMR (400 MHz, DMSO-$d_6$); 0.72 (t, 3H), 1.72 (q, 2H), 4.42 (t, 2H) 7.29–7.38 (m, 2H), 7.74–7.79 (m, 3H), 8.14 (q, 1H), 8.24 (q, 1), 8.48 (d, 1H), 8.60 (d, 1H), 8.76 (d, 1H) FAB MS; 461 ($M^+$+1)

EXAMPLE 12

Screening of Compounds which Inhibit the Increase of Intracellular $Ca^{++}$ Concentration Elicited by $LTC_4$ Using CHO Cells Stably Expressing $LTC_4$ Receptors $2\times10^4$ cells/well CHO cells stably expressing $LTC_4$ receptor prepared in Example 6 were inoculated to a 96 well Black/clear bottom plate, and after culturing for 24 hours, the medium was discarded, 100 µl/well of Hanks BSS containing 4 µM Fluo-3, AM (Molecular Probe), 0.004% pluronic acid, 1%, FBS, 20 mM HEPES, and 2.5 mM probenecid was added, then the cells were incubated at 37° C. for 1 hour. Candidate compounds of certain concentration were added, and after 5 minutes 1 nM $LTC_4$ was added. The changes of intracellular $Ca^{++}$ concentration were measured using FLIPR with the same condition as in Example 6. For example, compound A selected in Example 11 was revealed to be an antagonist of $LTC_4$ receptor, since it inhibited the increase of intracellular $Ca^{++}$ concentration of CHO cells stably expressing $LTC_4$ receptors elicited by $LTC_4$ in a dose-dependent manner. The IC50 was 2.3 µM. Moreover, the compound A also inhibited dose-dependently the increase of intracellular $Ca^{++}$ concentration of CHO cells stably expressing $LTC_4$ receptors elicited by $LTD_4$.

EXAMPLE 13

Figure 6:
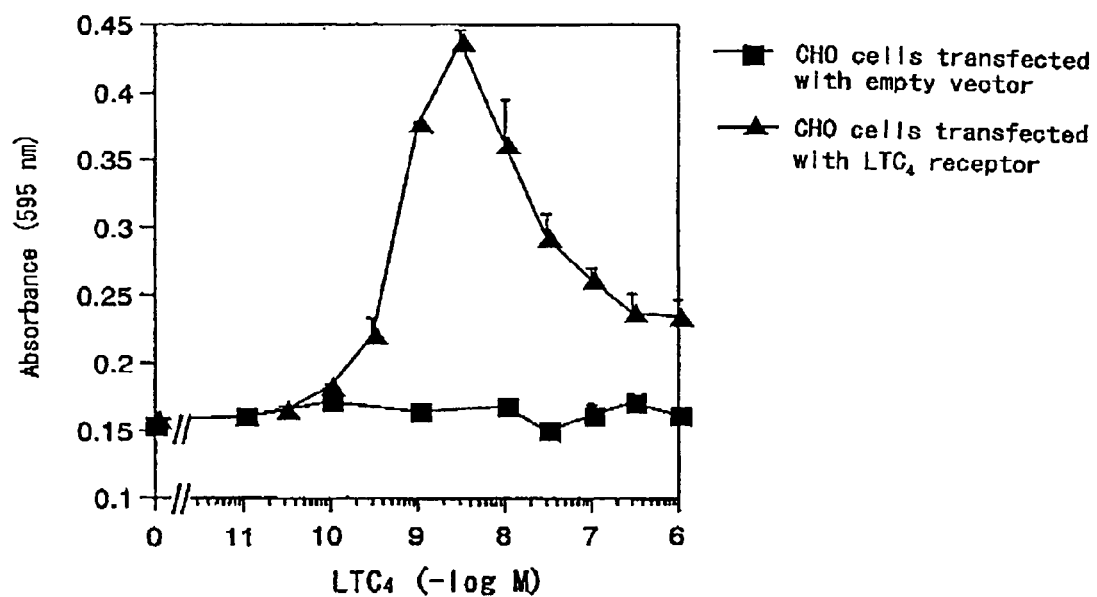
FIG. 6 shows the result of the dose dependency of $LTC_4$ to the cell migration of CHO cells expressing the $LTC_4$ receptors According to the figure, the vertical axis shows the absorbance (595 nm), and the horizontal axis shows the $LTC_4$ concentration in the reaction solution (-logM).
Figure 7:
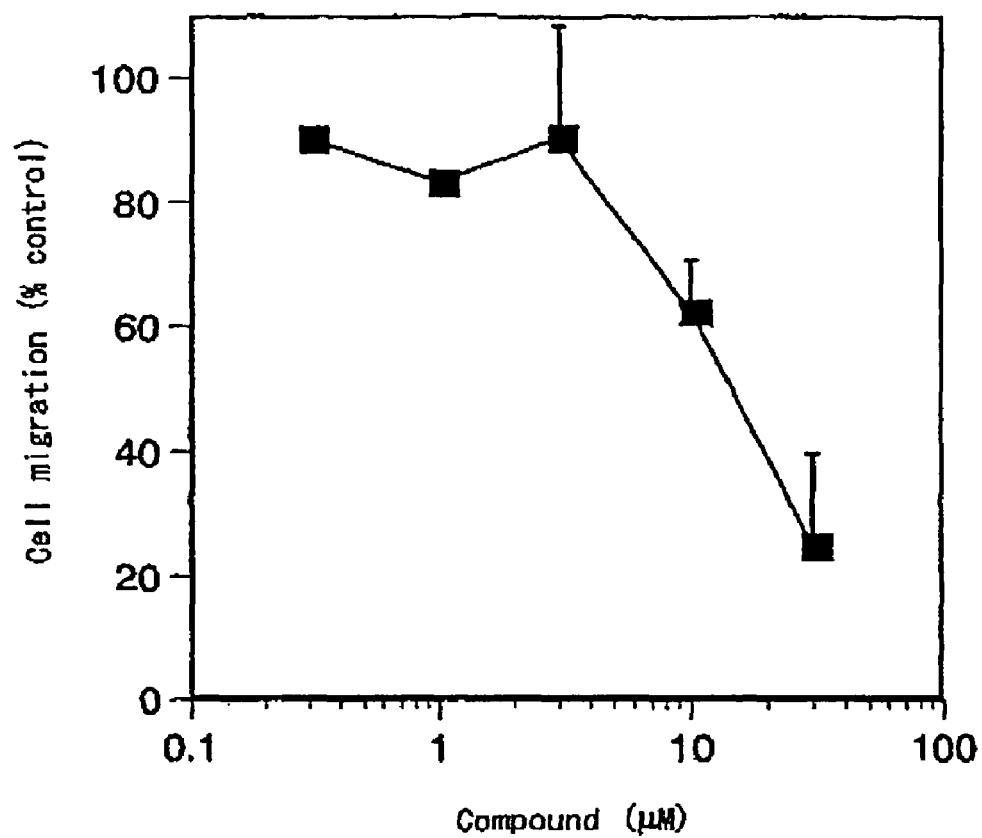
FIG. 7 shows the result of dose-dependent inhibition of compound A to the cell migration by $LTC_4$. According to the figure, the vertical axis shows the absorbance (%), herein the absorbance in the control without the compound is designated as 100%, and the horizontal axis shows the concentration of compound A in the reaction solution (μM).

Cell Migration of CHO Cells Expressing $LTC_4$ Receptors Elicited by $LTC_4$ and Inhibition by $LTC_4$ Receptor Antagonist 8 µm pore polycarbonate frame filter (Neuroprobe) was treated with 10 µg/ml fibronectin (Asahi techno glass)/PBS overnight at 4° C., 0 to 1 µM of $LTC_4$ was added to the lower layer of 96 blind well chamber (Neuroprobe) and the fibronectin treated frame filter was set. Then $2\times10^5$ cells of CHO cells expressing $LTC_4$ receptors and CHO cells into which empty vectors had been transfected were suspended in αMEM (without nucleic acid) medium/0.1% BSA, and inoculated to the upper layer of the chamber. After culturing for 4 hours in a $CO_2$ incubator at 37° C., the frame filter was fixed in methanol and stained with Diff-Quik staining kit (Kokusai-Shiyaku). The upper surface (the side onto which the cells were inoculated) of the filter was wiped, and after air drying, absorbance at 595 nm was measured with the plate reader (Molecular Devices). The result is shown in FIG. 6. Migration to the lower layer of the filter of CHO cells expressing $LTC_4$ receptors was observed by the addition of $LTC_4$. Bell-shaped chemotaxis was observed for the cell migration with the maximum migration activity at a $LTC_4$ concentration of 3 nM and the migration activity was inhibited at higher concentrations. The present $LTC_4$ receptor was revealed to have an activity to induce cell migration. Furthermore, cell migration activity was measured by adding a certain concentration of compound A selected in Example 11 to the upper layer and 3 nM $LTC_4$ to the lower layer of the cell migration system described above. Results are shown in FIG. 7. It has been revealed that this compound inhibits dose-dependently the cell migration by $LTC_4$. It is known that peptide leukotrienes induce cell migration of eosinophils and neutrophils (Spada, C. S., et al. J. Leukoc. Biol. (1994) 55, 183–191; Folco, F., et al. Novel Inhibitor of Leukotrienes (1999) 83–100, Birkhauser Verlag, Basel) and that of vascular endothelial cells (Kanayasu, T. et al. Biochem. Biophys. Res. Commun. (1989) 159, 572–578). The present $LTC_4$ receptor is expressed in eosinophils, neutrophils, and vascular endothelial cells as shown in Examples 8 and 9, and thus it was suggested that the present $LTC_4$ receptor is involved in exacerbation of inflammation and allergic symptoms such as asthma, through cell migration of these cells. Thus, the present antagonist of $LTC_4$ receptor is considered to have anti-inflammatory effect by inhibiting cell migration.

EXAMPLE 14

Increase of Intracellular $Ca^{++}$ Concentration by $LTC_4$ in Coronary Arterial Smooth Muscle Cells and Inhibition by $LTC_4$ Receptor Antagonist $4\times10^4$ cells/well of human coronary arterial smooth muscle cells, in which the expression of the present $LTC_4$ receptor was confirmed in Example 8, was inoculated to a 96 well Black/clear bottom plate, and after culturing for 24 hours, cells were washed, and following substitution of the medium with SmBM medium (Clonetics), was further cultured for 48 hours. The medium was discarded, and by adding 100 µl/well of Hanks BSS containing 4 µM Fluo-3, AM (Molecular Probe), 0.004% pluronic acid, 1% FBS, 20 mM HEPES, and 2.5 mM probenecid, the cells were incubated for 1 hour at 37° C. The changes of intracellular $Ca^{++}$ concentration by $LTC_4$ were measured using FLIPR at the same condition as in Example 6. As the result of measurement for 0, $10^{-6}$ to $10^{-9}$ M of $LTC_4$, $LTC_4$ was confirmed to induce increase of the intracellular $Ca^{++}$ concentration in a dose-dependent manner in the human coronary arterial smooth muscle cells. In the assay system described above, changes of intracellular $Ca^{++}$ concentration of coronary arterial smooth muscle cells by $LTC_4$ were measured after pre-treating 5 min with a certain concentration of compound A selected in Example 11, or Nifedipine (Funakoshi), a calcium channel blocker. Results are shown in FIG. 8. The compound was confirmed to inhibit dose-dependently the increase of intracellular $Ca^{++}$ concentration of coronary arterial smooth muscle cells by $LTC_4$. It is well known that the increase of intracellular $Ca^{++}$ concentration in blood vessel smooth muscle cells causes vasoconstriction (Bolton, T. B., et al. Physiol. Rev. (1979) 59, 606–718). Nifedipine is used as a therapeutic agent for angina pectoris and hypertension as a vasodilator, since it inhibits $Ca^{++}$ influx into blood vessel smooth muscle cells (Silver, P. J., Calcium Blockers. Mechanisms of Action and Clinical Applications. (1982) 37, Urban & Schwarzenberg, Baltimore). Nifedipine actually inhibited the increase of intracellular Cast concentration in the assay system described above. Thus, the $LTC_4$ receptor antagonist is considered to have a vasodilating activity by inhibiting the increase of intracellular $Ca^{++}$ concentration of blood vessel smooth muscle cells.

EXAMPLE 15

Cloning of Pig $LTC_4$ Receptor Gene cDNA was obtained by PCR using a combination of oligonucleotides shown in SEQ ID NO: 13 and 14, and a combination of oligonucleotide shown in SEQ ID NO: 15 and 16, designed based on the sequence information of gene PSEC0146 shown in SEQ ID NO: 1. PCR was carried out using pig genomic DNA obtained from pig skeletal muscle by using ISOTISSUE (Nippon Gene) as the template and Pyrobest DNA polymerase, under the existence of 5% DMSO, with 34 cycles of 98° C. (10 sec)/50° C. (30 sec)/72° C. (2 min). As a result, DNA fragments of about 1.0 kbp and 0.6 kbp were amplified respectively. The fragments were cloned into pCR-blunt (Invitrogen). The nucleotide sequences of the clones were determined by using ABI377 DNA Sequencer according to the dideoxy-terminator method. The nucleotide sequence revealed by contig of the results is shown in SEQ ID NO: 17. The sequence has an open reading frame of 1038 bases. Amino acid sequence estimated from the open reading frame (345 amino acids) is shown in SEQ ID NO: 18. The amino acid sequence showed a homology of 77.7% to the amino acid sequence of human $LTC_4$ receptor.

EXAMPLE 16

Cloning of Rat $LTC_4$ Receptor Gene

As the result of BLAST (Basic local alignment search tool) (S. F. Altschul et al., J. Mol. Biol., 215, 403–410 (1990)) search in GenBank using PSEC0146 gene sequence shown in SEQ ID NO: 1, EST (Expressed Sequence Tags) derived from rat spleen cDNA (Accession no. AI178926) was hit with a high score. cDNA was obtained by the PCRmethod using the oligonucleotide described in SEQ ID NO: 19 designed based on the sequence information of AI178926, which was expected to be the partial sequence of rat $LTC_4$ receptor gene, as a forward primer and the oligonucleotide described in SEQ ID NO: 20 designed from the gene sequence of PSEC1046 as a reverse primer. PCR was carried out by using rat spleen cDNA (Clontech) as the template and Pyrobest DNA polymerase, under the existence of 5% DMSO, with 34 cycles of 98° C. (10 sec)/55° C. (30 sec)/72° C. (2 min). As a result, a DNA fragment of about 1.3 kbp was amplified. The fragment was cloned into pCR-blunt, and the nucleotide sequences of obtained clones were determined by using ABI377 DNA Sequencer by the dideoxy-terminator method. The clarified nucleotide sequence is shown in SEQ ID NO: 21. The sequence has an open reading frame of 930 bases. The amino acid sequence estimated from the open reading frame (309 amino acids) is shown in SEQ ID NO: 22. The amino acid sequence was revealed to have a homology of 72.6% to the amino acid sequence of human $LTC_4$ receptor.

EXAMPLE 17

Expression of Pig $LTC_4$ Receptor, Binding Experiment with $LTC_4$, and Increase of Intracellular $Ca^{++}$ concentration by $LTC_4$ and $LTD_4$ The $LTC_4$ receptor activity of the protein encoded by the pig $LTC_4$ receptor DNA obtained in Example 15 was confirmed by experiments as follows. First, to express the protein encoded by the cDNA, the cDNA was obtained by PCR using pig genomic DNA as the template. The nucleotide sequence of primers required for PCR was designed based on the nucleotide sequence information determined in Example 15. The oligonucleotide indicated in SEQ ID NO: 23 and 24 were used as the forward primer and as the reverse primer, respectively in the PCR (a XbaI restriction site was added to the 5' end of each primer). PCR was carried out using Pyrobest DNA polymerase under the existence of 5% DMSO with 34 cycles of 98° C. (10 sec)/55° C. (30 sec)/72° C. (2 min) As a result, a DNA fragment of about 1.0 kbp was amplified. The fragment was digested with XbaI, and cloned into pEF-BOS. The resultant plasmid was used as pEF-BOS-pig $LTC_4$ receptor.

The membrane fraction of COS-1 cells into which pEF-BOS-pig $LTC_4$ receptor had been transfected was prepared under the same condition as in Example 4, and $[^3H]$-$LTC_4$ binding assay was carried out using 20 µg of the membrane fraction. The saturation curve of specific binding of $[^3H]$-$LTC_4$ toward the membrane fraction of COS-1 cells into which pEF-BOS-pig $LTC_4$ receptor had been transfected was plotted as in Example 5. As the result from the Scatchard analysis of the binding experiment, dissociation constant of $LTC_4$ binding toward the membrane fraction of COS-1 cells into which pEF-BOS-pig $LTC_4$ receptor had been transfected was Kd=2.89 nM, with a maximum binding of Bmax=0.25 pmol/mg protein.

Further, the changes of intracellular $Ca^{++}$ concentration were measured using HEK293-EBNA cells under the same condition as in Example 5. The dose-dependence of increase of intracellular $Ca^{++}$ concentration elicited by $LTC_4$ and $LTD_4$ in HEK293-EBNA cells, into which pEF-BOS-pig $LTC_4$ receptor had been transfected, was analyzed by the Logistic regression. As a result, it was revealed that the EC50 of $LTC_4$ is 5.0 nM and that of $LTD_4$ is 3.3 nM.

As described above, the present pig LTCG receptor was confirmed to have a high affinity to $LTC_4$, and induces increase of intracellular $Ca^{++}$ concentration dose-dependently in response to $LTC_4$ and $LTD_4$.

EXAMPLE 18

Expression of Rat $LTC_4$ Receptor and Changes of Intracellular $Ca^{++}$ Concentration by $LTC_4$ and $LTD_4$ The $LTC_4$ receptor activity of the protein encoded by rat $LTC_4$ receptor DNA obtained in Example 16 was confirmed by experiments as follows. The pCP-blunt in which rat $LTC_4$ receptor gene was cloned in Example 16 was digested with XbaI, and rat $LTC_4$ receptor DNA was cloned into pEF-BOS. This plasmid was designated as pEF-BOS-rat $LTC_4$ receptor.

The changes of intracellular $Ca^{++}$ concentration were measured using HEK293-EBNA cells under the same condition as in Example 5. Dose-dependence of the increase of intracellular $Ca^{++}$ concentration elicited by $LTC_4$ and $LTD_4$ in HEK293-EBNA cells, into which pEF-BOS-rat $LTC_4$ receptor had been transfected, was analyzed by Logistic regression. As a result, it was revealed that the EC50 of $LTC_4$ is 19 nM, and that of $LTD_4$ is 7.7 nM.

Thus, the present rat $LTC_4$ receptor was confirmed to induce the increase of intracellular $Ca^{++}$ concentration dose-dependently in response to $LTC_4$ and $LTD_4$.

INDUSTRIAL APPLICABILITY

The $LTC_4$ receptor provided by the present invention is useful for the identification and evaluation of drugs that act on the receptor as preventive and/or therapeutic agents of diseases caused by human $LTC_4$, for instance, inflammatory disease such as bronchitis and dermatitis, and diseases of cardiovascular system such as cardiac infarction. According to the present invention, $LTC_4$ receptor has become available to be used as purified protein or transformed cells that respond to $LTC_4$, and thus enables the in vitro binding experiment of $LTC_4$ receptor.

The in vitro binding experiment actualizes an ideal assay environment, excluding the effect of other proteins acting as $LTC_4$ receptor. Utilizing the screening method using the $LTC_4$ receptor provided in the present invention, useful compounds can be selected as therapeutic agents for diseases related to the receptor. Moreover, the DNA encoding the $LTC_4$ receptor of the present invention is not only useful for the production of $LTC_4$ receptors, but also are useful for diagnosis of diseases caused by mutations or abnormalities in the expression of the $LTC_4$ receptor. Moreover, the antibody recognizing the $LTC_4$ receptor can be used as drugs act on $LTC_4$ receptor, diagnostic, means for separation and purification of the polypeptides, and the like.

The invention claimed is:

1. An antibody against a protein comprising an amino acid sequence of any one of SEQ ID NO: 2, 18, and 22.

* * * * *

UNITED STATES PATENT AND TRADEMARK OFFICE
CERTIFICATE OF CORRECTION

PATENT NO.       : 7,217,800 B2
APPLICATION NO.  : 10/932004
DATED            : May 15, 2007
INVENTOR(S)      : Jun Takasaki et al.

It is certified that error appears in the above-identified patent and that said Letters Patent is hereby corrected as shown below:

On the Title page; item (73)

Assignee Name and Residence:

delete "2)HELIX RESEARCH INSTITUTE Chiba, Japan"

Signed and Sealed this

Ninth Day of October, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,217,800 B2 | Page 1 of 1 |
| APPLICATION NO. | : 10/932004 | |
| DATED | : May 15, 2007 | |
| INVENTOR(S) | : Jun Takasaki et al. | |

It is certified that error appears in the above-identified patent and that said Letters Patent is hereby corrected as shown below:

Col. 49, line 16, delete "comprising" and insert --consisting of--.

Signed and Sealed this

Twelfth Day of August, 2008

JON W. DUDAS
*Director of the United States Patent and Trademark Office*

SEQUENCE LISTING

<160> NUMBER OF SEQ ID NOS: 24

<210> SEQ ID NO 1
<211> LENGTH: 2807
<212> TYPE: DNA
<213> ORGANISM: Homo sapiens
<220> FEATURE:
<221> NAME/KEY: CDS
<222> LOCATION: (264)..(1301)
<223> OTHER INFORMATION:

<400> SEQUENCE: 1

```
aagttctcta agtttgaagc gtcagcttca accaaacaaa ttaatggcta ttctacattc      60
aaaaatcagg aaatttaaat ttattatgaa atgtaatgca gcatgtagta aagacttaac     120
cagtgtttta aaactcaact ttcaaagaaa agatagtatt gctccctgtt tcattaaaac     180
ctagagagat gtaatcagta agcaagaagg aaaaagggaa attcacaaag taacttttg      240 tgtctgtttc ttttaaccc agc atg gag aga aaa ttt atg tcc ttg caa cca     293
                         Met Glu Arg Lys Phe Met Ser Leu Gln Pro
                           1               5                  10 tcc atc tcc gta tca gaa atg gaa cca aat ggc acc ttc agc aat aac     341
Ser Ile Ser Val Ser Glu Met Glu Pro Asn Gly Thr Phe Ser Asn Asn
                 15                  20                  25 aac agc agg aac tgc aca att gaa aac ttc aag aga gaa ttt ttc cca     389
Asn Ser Arg Asn Cys Thr Ile Glu Asn Phe Lys Arg Glu Phe Phe Pro
         30                  35                  40 att gta tat ctg ata ata ttt ttc tgg gga gtc ttg gga aat ggg ttg     437
Ile Val Tyr Leu Ile Ile Phe Phe Trp Gly Val Leu Gly Asn Gly Leu
     45                  50                  55 tcc ata tat gtt ttc ctg cag cct tat aag aag tcc aca tct gtg aac     485
Ser Ile Tyr Val Phe Leu Gln Pro Tyr Lys Lys Ser Thr Ser Val Asn
 60                  65                  70 gtt ttc atg cta aat ctg gcc att tca gat ctc ctg ttc ata agc acg     533
Val Phe Met Leu Asn Leu Ala Ile Ser Asp Leu Leu Phe Ile Ser Thr
75                  80                  85                  90 ctt ccc ttc agg gct gac tat tat ctt aga ggc tcc aat tgg ata ttt     581
Leu Pro Phe Arg Ala Asp Tyr Tyr Leu Arg Gly Ser Asn Trp Ile Phe
                 95                 100                 105 gga gac ctg gcc tgc agg att atg tct tat tcc ttg tat gtc aac atg     629
Gly Asp Leu Ala Cys Arg Ile Met Ser Tyr Ser Leu Tyr Val Asn Met
        110                 115                 120 tac agc agt att tat ttc ctg acc gtg ctg agt gtt gtg cgt ttc ctg     677
Tyr Ser Ser Ile Tyr Phe Leu Thr Val Leu Ser Val Val Arg Phe Leu
    125                 130                 135 gca atg gtt cac ccc ttt cgg ctt ctg cat gtc acc agc atc agg agt     725
Ala Met Val His Pro Phe Arg Leu Leu His Val Thr Ser Ile Arg Ser
    140                 145                 150 gcc tgg atc ctc tgt ggg atc ata tgg atc ctt atc atg gct tcc tca     773
Ala Trp Ile Leu Cys Gly Ile Ile Trp Ile Leu Ile Met Ala Ser Ser
155                 160                 165                 170 ata atg ctc ctg gac agt ggc tct gag cag aac ggc agt gtc aca tca     821
Ile Met Leu Leu Asp Ser Gly Ser Glu Gln Asn Gly Ser Val Thr Ser
                175                 180                 185 tgc tta gag ctg aat ctc tat aaa att gct aag ctg cag acc atg aac     869
Cys Leu Glu Leu Asn Leu Tyr Lys Ile Ala Lys Leu Gln Thr Met Asn
        190                 195                 200 tat att gcc ttg gtg gtg ggc tgc ctg ctg cca ttt ttc aca ctc agc     917
Tyr Ile Ala Leu Val Val Gly Cys Leu Leu Pro Phe Phe Thr Leu Ser
    205                 210                 215
```

-continued

| | | |
|---|---|---|
| atc tgt tat ctg ctg atc att cgg gtt ctg tta aaa gtg gag gtc cca<br>Ile Cys Tyr Leu Leu Ile Ile Arg Val Leu Leu Lys Val Glu Val Pro<br>220                           225                      230 | | 965 |
| gaa tcg ggg ctg cgg gtt tct cac agg aag gca ctg acc acc atc atc<br>Glu Ser Gly Leu Arg Val Ser His Arg Lys Ala Leu Thr Thr Ile Ile<br>235                         240                   245                      250 | | 1013 |
| atc acc ttg atc atc ttc ttc ttg tgt ttc ctg ccc tat cac aca ctg<br>Ile Thr Leu Ile Ile Phe Phe Leu Cys Phe Leu Pro Tyr His Thr Leu<br>                     255                     260                     265 | | 1061 |
| agg acc gtc cac ttg acg aca tgg aaa gtg ggt tta tgc aaa gac aga<br>Arg Thr Val His Leu Thr Thr Trp Lys Val Gly Leu Cys Lys Asp Arg<br> 270                          275                     280 | | 1109 |
| ctg cat aaa gct ttg gtt atc aca ctg gcc ttg gca gca gcc aat gcc<br>Leu His Lys Ala Leu Val Ile Thr Leu Ala Leu Ala Ala Ala Asn Ala<br>             285                     290                     295 | | 1157 |
| tgc ttc aat cct ctg ctc tat tac ttt gct ggg gag aat ttt aag gac<br>Cys Phe Asn Pro Leu Leu Tyr Tyr Phe Ala Gly Glu Asn Phe Lys Asp<br>300                          305                   310 | | 1205 |
| aga cta aag tct gca ctc aga aaa ggc cat cca cag aag gca aag aca<br>Arg Leu Lys Ser Ala Leu Arg Lys Gly His Pro Gln Lys Ala Lys Thr<br>315                       320                   325                 330 | | 1253 |
| aag tgt gtt ttc cct gtt agt gtg tgg ttg aga aag gaa aca aga gta<br>Lys Cys Val Phe Pro Val Ser Val Trp Leu Arg Lys Glu Thr Arg Val<br>                     335                     340                 345 | | 1301 |
| taaggagctc ttagatgaga cctgttcttg tatccttgtg tccatcttca ttcactcata | | 1361 |
| gtctccaaat gactttgtat ttacatcact cccaacaaat gttgattctt aatatttagt | | 1421 |
| tgaccattac ttttgttaat aagacctact tcaaaaattt tattcagtgt attttcagtt | | 1481 |
| gttgagtctt aatgagggat acaggaggaa aaatccctac tagagtcctg tgggctgaaa | | 1541 |
| tatcagactg ggaaaaaatg caaagcacat tggatcctac ttttcttcag atattgaacc | | 1601 |
| agatctctgg cccatcaggc tttctaaatt cttcaaaaga gccacaactt ccccagcttc | | 1661 |
| tccagctccc ctgtcctctt caatcccttg agatatagca actaacgacg ctactggaag | | 1721 |
| ccccagagca gaaagaagc acatcctaag attcagggaa agactaactg tgaaaaggaa | | 1781 |
| ggctgtccta taacaaagca gcatcaagtc ccaagtaagg acagtgagag aaaagggga | | 1841 |
| gaaggattgg agcaaaagag aactggcaat aagtagggga aggaagaatt tcattttgca | | 1901 |
| ttgggagaga ggttctaaca cactgaaggc aaccctattt ctactgtttc tctcttgcca | | 1961 |
| gggtattagg aaggacagga aaagtaggag gaggatctgg ggcattgccc taggaaatga | | 2021 |
| aagaattgtg tatagaatgg aaggggatc atcaaggaca tgtatctcaa attttctttg | | 2081 |
| agatgcaggt tagttgacct tgctgcagtt ctccttccca ttaattcatt gggatggaag | | 2141 |
| ccaaaaataa aagaggtgcc tctgaggatt agggttgagc actcaaggga agatggagt | | 2201 |
| agagggcaaa tagcaaaagt tgttgcactc ctgaaattct attaacattt ccgcagaaga | | 2261 |
| tgagtaggga gatgctgcct tccctttga gatagtgtat aaaaacacta gatagtgtga | | 2321 |
| gaggttcctt tctgtccatt gaaacaaggc taaggatact accaactact atcaccatga | | 2381 |
| ccattgtact gacaacaatt gaatgcagtc tccctgcagg gcagattatg ccaggcactt | | 2441 |
| tacatttgtt gatcccattt gacattcaca ccaaagctct gagttccatt ttacagctga | | 2501 |
| agaaattgaa gcttagagaa attaagaagc ttgtttaagt ttacacagct agtaagagtt | | 2561 |
| ttaaaaatct ctgtgcagaa gtgttggctg ggtgctctcc ccaccactac ccttgtaaac | | 2621 |
| ttccaggaag attggttgaa agtctgaata aaagctgtcc tttcctacca atttcctccc | | 2681 |
| cctcctcact ctcacaagaa aaccaaaagt ttctcttcag agttgttgac tcatagtaca | | 2741 |

-continued

```
gtaaaggtg gaggtgatat ggcattctga aagtagggag ggactaagtc agtcgtcata    2801
ctaaac                                                              2807
```

<210> SEQ ID NO 2
<211> LENGTH: 346
<212> TYPE: PRT
<213> ORGANISM: Homo sapiens

<400> SEQUENCE: 2

```
Met Glu Arg Lys Phe Met Ser Leu Gln Pro Ser Ile Ser Val Ser Glu
1               5                   10                  15

Met Glu Pro Asn Gly Thr Phe Ser Asn Asn Ser Arg Asn Cys Thr
            20                  25                  30

Ile Glu Asn Phe Lys Arg Glu Phe Phe Pro Ile Val Tyr Leu Ile Ile
            35                  40                  45

Phe Phe Trp Gly Val Leu Gly Asn Gly Leu Ser Ile Tyr Val Phe Leu
        50                  55                  60

Gln Pro Tyr Lys Lys Ser Thr Ser Val Asn Val Phe Met Leu Asn Leu
65                  70                  75                  80

Ala Ile Ser Asp Leu Leu Phe Ile Ser Thr Leu Pro Phe Arg Ala Asp
                85                  90                  95

Tyr Tyr Leu Arg Gly Ser Asn Trp Ile Phe Gly Asp Leu Ala Cys Arg
            100                 105                 110

Ile Met Ser Tyr Ser Leu Tyr Val Asn Met Tyr Ser Ser Ile Tyr Phe
        115                 120                 125

Leu Thr Val Leu Ser Val Val Arg Phe Leu Ala Met Val His Pro Phe
    130                 135                 140

Arg Leu Leu His Val Thr Ser Ile Arg Ser Ala Trp Ile Leu Cys Gly
145                 150                 155                 160

Ile Ile Trp Ile Leu Ile Met Ala Ser Ser Ile Met Leu Leu Asp Ser
                165                 170                 175

Gly Ser Glu Gln Asn Gly Ser Val Thr Ser Cys Leu Glu Leu Asn Leu
            180                 185                 190

Tyr Lys Ile Ala Lys Leu Gln Thr Met Asn Tyr Ile Ala Leu Val Val
        195                 200                 205

Gly Cys Leu Leu Pro Phe Phe Thr Leu Ser Ile Cys Tyr Leu Leu Ile
    210                 215                 220

Ile Arg Val Leu Leu Lys Val Glu Val Pro Glu Ser Gly Leu Arg Val
225                 230                 235                 240

Ser His Arg Lys Ala Leu Thr Thr Ile Ile Thr Leu Ile Ile Phe
                245                 250                 255

Phe Leu Cys Phe Leu Pro Tyr His Thr Leu Arg Thr Val His Leu Thr
            260                 265                 270

Thr Trp Lys Val Gly Leu Cys Lys Asp Arg Leu His Lys Ala Leu Val
        275                 280                 285

Ile Thr Leu Ala Leu Ala Ala Ala Asn Ala Cys Phe Asn Pro Leu Leu
    290                 295                 300

Tyr Tyr Phe Ala Gly Glu Asn Phe Lys Asp Arg Leu Lys Ser Ala Leu
305                 310                 315                 320

Arg Lys Gly His Pro Gln Lys Ala Lys Thr Lys Cys Val Phe Pro Val
                325                 330                 335

Ser Val Trp Leu Arg Lys Glu Thr Arg Val
            340                 345
```

<210> SEQ ID NO 3
<211> LENGTH: 30
<212> TYPE: RNA
<213> ORGANISM: Artificial Sequence
<220> FEATURE:
<223> OTHER INFORMATION: artificially synthesized oligo-cap linker
      sequence

<400> SEQUENCE: 3
agcaucgagu cggccuuguu ggccuacugg                              30

<210> SEQ ID NO 4
<211> LENGTH: 42
<212> TYPE: DNA
<213> ORGANISM: Artificial Sequence
<220> FEATURE:
<223> OTHER INFORMATION: artificially synthesized oligo (dT) primer
      sequence

<400> SEQUENCE: 4
gcggctgaag acggcctatg tggccttttt tttttttttt tt                42

<210> SEQ ID NO 5
<211> LENGTH: 21
<212> TYPE: DNA
<213> ORGANISM: Artificial Sequence
<220> FEATURE:
<223> OTHER INFORMATION: artificially synthesized primer sequence

<400> SEQUENCE: 5
agcatcgagt cggcctttgtt g                                      21

<210> SEQ ID NO 6
<211> LENGTH: 21
<212> TYPE: DNA
<213> ORGANISM: Artificial Sequence
<220> FEATURE:
<223> OTHER INFORMATION: artificially synthesized primer sequence

<400> SEQUENCE: 6
gcggctgaag acggcctatg t                                       21

<210> SEQ ID NO 7
<211> LENGTH: 34
<212> TYPE: DNA
<213> ORGANISM: Artificial Sequence
<220> FEATURE:
<223> OTHER INFORMATION: artificially synthesized primer sequence

<400> SEQUENCE: 7
gggtctagaa tggagagaaa atttatgtcc ttgc                         34

<210> SEQ ID NO 8
<211> LENGTH: 40
<212> TYPE: DNA
<213> ORGANISM: Artificial Sequence
<220> FEATURE:
<223> OTHER INFORMATION: artificially synthesized primer sequence

<400> SEQUENCE: 8
gggtctagac tattatactc ttgtttcctt tctcaaccac                   40

<210> SEQ ID NO 9
<211> LENGTH: 24
<212> TYPE: DNA
<213> ORGANISM: Artificial Sequence

```
<220> FEATURE:
<223> OTHER INFORMATION: artificially synthesized primer sequence

<400> SEQUENCE: 9
tggatcctct gtgggatcat atgg                                          24

<210> SEQ ID NO 10
<211> LENGTH: 25
<212> TYPE: DNA
<213> ORGANISM: Artificial Sequence
<220> FEATURE:
<223> OTHER INFORMATION: artificially synthesized primer sequence

<400> SEQUENCE: 10
aattctcccc agcaaagtaa tagag                                         25

<210> SEQ ID NO 11
<211> LENGTH: 30
<212> TYPE: DNA
<213> ORGANISM: Artificial Sequence
<220> FEATURE:
<223> OTHER INFORMATION: artificially synthesized primer sequence

<400> SEQUENCE: 11
gttaaaagtg gaggtcccag aatcggggct                                    30

<210> SEQ ID NO 12
<211> LENGTH: 30
<212> TYPE: DNA
<213> ORGANISM: Artificial Sequence
<220> FEATURE:
<223> OTHER INFORMATION: artificially synthesized primer sequence

<400> SEQUENCE: 12
agaaagcctg atgggccaga gatctggttc                                    30

<210> SEQ ID NO 13
<211> LENGTH: 27
<212> TYPE: DNA
<213> ORGANISM: Artificial Sequence
<220> FEATURE:
<223> OTHER INFORMATION: artificially synthesized primer sequence

<400> SEQUENCE: 13
cacaaagtaa cttttttgtgt ctgtttc                                      27

<210> SEQ ID NO 14
<211> LENGTH: 23
<212> TYPE: DNA
<213> ORGANISM: Artificial Sequence
<220> FEATURE:
<223> OTHER INFORMATION: artificially synthesized primer sequence

<400> SEQUENCE: 14
ttctccccag caaagtaata gag                                           23

<210> SEQ ID NO 15
<211> LENGTH: 24
<212> TYPE: DNA
<213> ORGANISM: Artificial Sequence
<220> FEATURE:
<223> OTHER INFORMATION: artificially synthesized primer sequence

<400> SEQUENCE: 15
tggatcctct gtgggatcat atgg                                          24
```

```
<210> SEQ ID NO 16
<211> LENGTH: 17
<212> TYPE: DNA
<213> ORGANISM: Artificial Sequence
<220> FEATURE:
<223> OTHER INFORMATION: artificially synthesized primer sequence

<400> SEQUENCE: 16
aacaggtctc atctaag                                                17

<210> SEQ ID NO 17
<211> LENGTH: 1101
<212> TYPE: DNA
<213> ORGANISM: Sus scrofa
<220> FEATURE:
<221> NAME/KEY: CDS
<222> LOCATION: (14)..(1048)
<223> OTHER INFORMATION:

<400> SEQUENCE: 17
tttttaattc agc atg gag aga aaa ctt atg tcc tta ctt cca tcc atc     49
            Met Glu Arg Lys Leu Met Ser Leu Leu Pro Ser Ile
              1               5                  10 tcc cta tca gaa atg gaa ccc aat agt acc ttg ggc aat cac aat agc    97
Ser Leu Ser Glu Met Glu Pro Asn Ser Thr Leu Gly Asn His Asn Ser
         15                  20                  25 aac agg agc tgc acc aca gaa aac ttc aag aga gaa ttt tac ccc att   145
Asn Arg Ser Cys Thr Thr Glu Asn Phe Lys Arg Glu Phe Tyr Pro Ile
 30                  35                  40 gtg tac cta gta ata ttt atc tgg gga gcc ttg gga aat ggc ttt tct   193
Val Tyr Leu Val Ile Phe Ile Trp Gly Ala Leu Gly Asn Gly Phe Ser
 45                  50                  55                  60 ata tat gtt ttc ctg aaa cct tat aag aag tcc aca tca gtc aat gtt   241
Ile Tyr Val Phe Leu Lys Pro Tyr Lys Lys Ser Thr Ser Val Asn Val
             65                  70                  75 ttc atg cta aat ctg gcc att tcg gat ctc tta ttc aca atc aca ctg   289
Phe Met Leu Asn Leu Ala Ile Ser Asp Leu Leu Phe Thr Ile Thr Leu
             80                  85                  90 ccc ttc agg gtt gac tat tac ctt aga ggc tcc aac ygg ata ttt ggg   337
Pro Phe Arg Val Asp Tyr Tyr Leu Arg Gly Ser Asn Xaa Ile Phe Gly
         95                 100                 105 gac aca cct tgc agg att atg tct tat tct atg tat gtc aac atg tac   385
Asp Thr Pro Cys Arg Ile Met Ser Tyr Ser Met Tyr Val Asn Met Tyr
     110                 115                 120 agc agc att tat ttc ctg act gtg ctg agt gtt gtg cgt ttc ctg gca   433
Ser Ser Ile Tyr Phe Leu Thr Val Leu Ser Val Val Arg Phe Leu Ala
125                 130                 135                 140 act gtt cac ccc ttc cgg ctc ctt cat acc acc agc atc aag aac gcc   481
Thr Val His Pro Phe Arg Leu Leu His Thr Thr Ser Ile Lys Asn Ala
                145                 150                 155 tgg att ctc tgt ggg gtc ata tgg atc ttt att atg gct tcc tca aca   529
Trp Ile Leu Cys Gly Val Ile Trp Ile Phe Ile Met Ala Ser Ser Thr
            160                 165                 170 gta ctt ctg aag aat ggc tct gag cag aaa gac aat gtc aca ttg tgc   577
Val Leu Leu Lys Asn Gly Ser Glu Gln Lys Asp Asn Val Thr Leu Cys
        175                 180                 185 tta gag ctg aat tct aat aaa gtt act aaa ctg aag acc atg aac tac   625
Leu Glu Leu Asn Ser Asn Lys Val Thr Lys Leu Lys Thr Met Asn Tyr
    190                 195                 200 gtt gcc ttg gtg gtg ggc ttt gtg ctg cca ttc ggc act ctc agc atc   673
Val Ala Leu Val Val Gly Phe Val Leu Pro Phe Gly Thr Leu Ser Ile
205                 210                 215                 220
```

```
tgc tac ctg cta atc att cga gct ttg tta aag gta gag gtc ccg gag      721
Cys Tyr Leu Leu Ile Ile Arg Ala Leu Leu Lys Val Glu Val Pro Glu
            225                 230                 235 tcc ggg ctg cgg ctt tct cac agg aag gca ttg atc acc gtc atc att      769
Ser Gly Leu Arg Leu Ser His Arg Lys Ala Leu Ile Thr Val Ile Ile
        240                 245                 250 gct ttg atc atc ttt ctc ctg tgt ttc ctg ccc tat cac gta ctg aga      817
Ala Leu Ile Ile Phe Leu Leu Cys Phe Leu Pro Tyr His Val Leu Arg
    255                 260                 265 acc ctt cac ctg ctc gaa tgg aaa gct gat aaa tgc aaa gac agg ctg      865
Thr Leu His Leu Leu Glu Trp Lys Ala Asp Lys Cys Lys Asp Arg Leu
270                 275                 280 cat aaa gct gtg gct gtc aca cta gct ttg gca gcg gcc aac agc tgc      913
His Lys Ala Val Ala Val Thr Leu Ala Leu Ala Ala Ala Asn Ser Cys
285                 290                 295                 300 ttc aat cct ttc ctc tat tac ttt gct ggg gag aat ttt aag gac aga      961
Phe Asn Pro Phe Leu Tyr Tyr Phe Ala Gly Glu Asn Phe Lys Asp Arg
            305                 310                 315 cta aag tct gca ctc agg aaa ggt cga cca cag aaa aca agg tgc ggt     1009
Leu Lys Ser Ala Leu Arg Lys Gly Arg Pro Gln Lys Thr Arg Cys Gly
        320                 325                 330 ttc tct gtc tgt gtg tgg ctg aaa aag gaa acg aga gtg taagggatta     1058
Phe Ser Val Cys Val Trp Leu Lys Lys Glu Thr Arg Val
    335                 340                 345 ttaggtgagg ctgttattat gtccttgccc ttgtgtctac ccc                    1101

<210> SEQ ID NO 18
<211> LENGTH: 345
<212> TYPE: PRT
<213> ORGANISM: Sus scrofa
<220> FEATURE:
<221> NAME/KEY: misc_feature
<222> LOCATION: (105)..(105)
<223> OTHER INFORMATION: The 'Xaa' at location 105 stands for Arg, or
      Trp.

<400> SEQUENCE: 18

Met Glu Arg Lys Leu Met Ser Leu Leu Pro Ser Ile Ser Leu Ser Glu
1               5                   10                  15

Met Glu Pro Asn Ser Thr Leu Gly Asn His Asn Ser Asn Arg Ser Cys
            20                  25                  30

Thr Thr Glu Asn Phe Lys Arg Glu Phe Tyr Pro Ile Val Tyr Leu Val
        35                  40                  45

Ile Phe Ile Trp Gly Ala Leu Gly Asn Gly Phe Ser Ile Tyr Val Phe
    50                  55                  60

Leu Lys Pro Tyr Lys Lys Ser Thr Ser Val Asn Val Phe Met Leu Asn
65                  70                  75                  80

Leu Ala Ile Ser Asp Leu Leu Phe Thr Ile Thr Leu Pro Phe Arg Val
                85                  90                  95

Asp Tyr Tyr Leu Arg Gly Ser Asn Xaa Ile Phe Gly Asp Thr Pro Cys
            100                 105                 110

Arg Ile Met Ser Tyr Ser Met Tyr Val Asn Met Tyr Ser Ser Ile Tyr
        115                 120                 125

Phe Leu Thr Val Leu Ser Val Val Arg Phe Leu Ala Thr Val His Pro
    130                 135                 140

Phe Arg Leu Leu His Thr Thr Ser Ile Lys Asn Ala Trp Ile Leu Cys
145                 150                 155                 160

Gly Val Ile Trp Ile Phe Ile Met Ala Ser Ser Thr Val Leu Leu Lys
                165                 170                 175
```

```
Asn Gly Ser Glu Gln Lys Asp Asn Val Thr Leu Cys Leu Glu Leu Asn
            180                 185                 190

Ser Asn Lys Val Thr Lys Leu Lys Thr Met Asn Tyr Val Ala Leu Val
        195                 200                 205

Val Gly Phe Val Leu Pro Phe Gly Thr Leu Ser Ile Cys Tyr Leu Leu
    210                 215                 220

Ile Ile Arg Ala Leu Leu Lys Val Glu Val Pro Glu Ser Gly Leu Arg
225                 230                 235                 240

Leu Ser His Arg Lys Ala Leu Ile Thr Val Ile Ala Leu Ile Ile
            245                 250                 255

Phe Leu Leu Cys Phe Leu Pro Tyr His Val Leu Arg Thr Leu His Leu
            260                 265                 270

Leu Glu Trp Lys Ala Asp Lys Cys Lys Asp Arg Leu His Lys Ala Val
            275                 280                 285

Ala Val Thr Leu Ala Leu Ala Ala Asn Ser Cys Phe Asn Pro Phe
    290                 295                 300

Leu Tyr Tyr Phe Ala Gly Glu Asn Phe Lys Asp Arg Leu Lys Ser Ala
305                 310                 315                 320

Leu Arg Lys Gly Arg Pro Gln Lys Thr Arg Cys Gly Phe Ser Val Cys
            325                 330                 335

Val Trp Leu Lys Lys Glu Thr Arg Val
            340                 345
```

<210> SEQ ID NO 19
<211> LENGTH: 20
<212> TYPE: DNA
<213> ORGANISM: Artificial Sequence
<220> FEATURE:
<223> OTHER INFORMATION: artificially synthesized primer sequence

<400> SEQUENCE: 19
atatgtctga tgcctgccaa                                          20

<210> SEQ ID NO 20
<211> LENGTH: 22
<212> TYPE: DNA
<213> ORGANISM: Artificial Sequence
<220> FEATURE:
<223> OTHER INFORMATION: artificially synthesized primer sequence

<400> SEQUENCE: 20
agtcatttgg agactatgag tg                                       22

<210> SEQ ID NO 21
<211> LENGTH: 1249
<212> TYPE: DNA
<213> ORGANISM: Rattus norvegicus
<220> FEATURE:
<221> NAME/KEY: CDS
<222> LOCATION: (208)..(1134)
<223> OTHER INFORMATION:

<400> SEQUENCE: 21
atatgtctga tgcctgccaa ggtcagaaga gggtgtcgga gaaacttgct tctcgccatg     60
tgagatggag tacggcaaat gtttgatcac taatcaggaa gaaaagtgga attgtatgaa    120 gtaactttt gggtttattt cttttaaac taatataaag agaaaacttt atattagtcc     180
ttgcctctgt ccaactccat attagaa atg gga gta act ggg acc ccc agc tat    234
                              Met Gly Val Thr Gly Thr Pro Ser Tyr
                               1               5

-continued

| | | |
|---|---|---|
| tat agt gac aag aac tgt aca ata gaa aac ttc aag agg gac ttt tac<br>Tyr Ser Asp Lys Asn Cys Thr Ile Glu Asn Phe Lys Arg Asp Phe Tyr<br>10                 15                    20                 25 | 282 |
| cct atc atc tac ctg ata ata ttt gtc tgg gga gcc ttg gga aat ggc<br>Pro Ile Ile Tyr Leu Ile Ile Phe Val Trp Gly Ala Leu Gly Asn Gly<br>                30                    35                 40 | 330 |
| ttt tcc ata tat gtc ttc cta cag act tac aag aag tcc aca tct gtg<br>Phe Ser Ile Tyr Val Phe Leu Gln Thr Tyr Lys Lys Ser Thr Ser Val<br>              45                    50                  55 | 378 |
| aat gtt ttc atg ctc aac ctg gcc att tca gat ttc cta ttc ata agc<br>Asn Val Phe Met Leu Asn Leu Ala Ile Ser Asp Phe Leu Phe Ile Ser<br>    60                    65                    70 | 426 |
| acc ctg ccc ttc agg gct gac tat aat ttc aga ggt tct gat tgg ata<br>Thr Leu Pro Phe Arg Ala Asp Tyr Asn Phe Arg Gly Ser Asp Trp Ile<br>75                 80                    85 | 474 |
| ttt ggg gac tgg gcc tgc aga att atg tct tat tct tta tat gtc aac<br>Phe Gly Asp Trp Ala Cys Arg Ile Met Ser Tyr Ser Leu Tyr Val Asn<br>90                 95                   100             105 | 522 |
| atg tat act agc att tat ttc cta act gtg ctg agt att gtg cgc ttc<br>Met Tyr Thr Ser Ile Tyr Phe Leu Thr Val Leu Ser Ile Val Arg Phe<br>                    110                 115              120 | 570 |
| ctg gcc act gcc cac ccc ttc cag atg ctc cat atc acc agc gtt agg<br>Leu Ala Thr Ala His Pro Phe Gln Met Leu His Ile Thr Ser Val Arg<br>              125                 130               135 | 618 |
| agt gcc tgg atc ctc tgt ggg att ata tgg gtc ttc atc atg gct tcc<br>Ser Ala Trp Ile Leu Cys Gly Ile Ile Trp Val Phe Ile Met Ala Ser<br>         140                    145                 150 | 666 |
| tca gga ctg ctt ctg aag cat ggc caa gag aag aaa aat aac act aca<br>Ser Gly Leu Leu Leu Lys His Gly Gln Glu Lys Lys Asn Asn Thr Thr<br>155                  160                 165 | 714 |
| ttg tgc ttt gag ctg aat ctc caa aag ttt aaa aat ctc gtc atc ttg<br>Leu Cys Phe Glu Leu Asn Leu Gln Lys Phe Lys Asn Leu Val Ile Leu<br>170                 175                 180               185 | 762 |
| aac tac att gca tta ggg gtg ggc ttc ctt cca ttt ttc ata ctc<br>Asn Tyr Ile Ala Leu Gly Val Gly Phe Leu Leu Pro Phe Phe Ile Leu<br>              190                 195               200 | 810 |
| acc atc tgc tac ctg ttg atc atc cgg gtc ttg tta aag gtg gag att<br>Thr Ile Cys Tyr Leu Leu Ile Ile Arg Val Leu Leu Lys Val Glu Ile<br>         205                    210               215 | 858 |
| cca gaa tca ggt cca cgg gat gct cag agg aag gca ctg act act atc<br>Pro Glu Ser Gly Pro Arg Asp Ala Gln Arg Lys Ala Leu Thr Thr Ile<br>              220                 225               230 | 906 |
| gtc att gcc atg atc atc ttc ctc ctc tgt ttt ctg cca tac cat gca<br>Val Ile Ala Met Ile Ile Phe Leu Leu Cys Phe Leu Pro Tyr His Ala<br>235                  240                 245 | 954 |
| ctt cgg acc atc cac ttg gtc aca tgg gat gca gat tca tgt atg gat<br>Leu Arg Thr Ile His Leu Val Thr Trp Asp Ala Asp Ser Cys Met Asp<br>250                 255                 260               265 | 1002 |
| gaa tta cat aag gcc acg gtc atc act ctg acc ttg gct gca gcc aac<br>Glu Leu His Lys Ala Thr Val Ile Thr Leu Thr Leu Ala Ala Ala Asn<br>              270                 275               280 | 1050 |
| agc tgc ttc aat ccc ttt ctc tat tat ttt gct gga gag aat ttc aaa<br>Ser Cys Phe Asn Pro Phe Leu Tyr Tyr Phe Ala Gly Glu Asn Phe Lys<br>                    285                 290               295 | 1098 |
| gca cga tta agg gct ata ttc agc aaa gat cat cta tagaaagcaa<br>Ala Arg Leu Arg Ala Ile Phe Ser Lys Asp His Leu<br>         300                    305 | 1144 |
| agtcaaagtg cagccttcct atttgtgtat tactgaagac cagagttaag agcataaggg | 1204 |
| gctgttctgg aggtacgctc atgaacactg gtgtccacct tcact | 1249 |

```
<210> SEQ ID NO 22
<211> LENGTH: 309
<212> TYPE: PRT
<213> ORGANISM: Rattus norvegicus

<400> SEQUENCE: 22

Met Gly Val Thr Gly Thr Pro Ser Tyr Tyr Ser Asp Lys Asn Cys Thr
1               5                   10                  15

Ile Glu Asn Phe Lys Arg Asp Phe Tyr Pro Ile Ile Tyr Leu Ile Ile
            20                  25                  30

Phe Val Trp Gly Ala Leu Gly Asn Gly Phe Ser Ile Tyr Val Phe Leu
        35                  40                  45

Gln Thr Tyr Lys Lys Ser Thr Ser Val Asn Val Phe Met Leu Asn Leu
    50                  55                  60

Ala Ile Ser Asp Phe Leu Phe Ile Ser Thr Leu Pro Phe Arg Ala Asp
65                  70                  75                  80

Tyr Asn Phe Arg Gly Ser Asp Trp Ile Phe Gly Asp Trp Ala Cys Arg
                85                  90                  95

Ile Met Ser Tyr Ser Leu Tyr Val Asn Met Tyr Thr Ser Ile Tyr Phe
            100                 105                 110

Leu Thr Val Leu Ser Ile Val Arg Phe Leu Ala Thr Ala His Pro Phe
        115                 120                 125

Gln Met Leu His Ile Thr Ser Val Arg Ser Ala Trp Ile Leu Cys Gly
    130                 135                 140

Ile Ile Trp Val Phe Ile Met Ala Ser Ser Gly Leu Leu Leu Lys His
145                 150                 155                 160

Gly Gln Glu Lys Lys Asn Asn Thr Thr Leu Cys Phe Glu Leu Asn Leu
                165                 170                 175

Gln Lys Phe Lys Asn Leu Val Ile Leu Asn Tyr Ile Ala Leu Gly Val
            180                 185                 190

Gly Phe Leu Leu Pro Phe Phe Ile Leu Thr Ile Cys Tyr Leu Leu Ile
        195                 200                 205

Ile Arg Val Leu Leu Lys Val Glu Ile Pro Glu Ser Gly Pro Arg Asp
    210                 215                 220

Ala Gln Arg Lys Ala Leu Thr Thr Ile Val Ile Ala Met Ile Ile Phe
225                 230                 235                 240

Leu Leu Cys Phe Leu Pro Tyr His Ala Leu Arg Thr Ile His Leu Val
                245                 250                 255

Thr Trp Asp Ala Asp Ser Cys Met Asp Glu Leu His Lys Ala Thr Val
            260                 265                 270

Ile Thr Leu Thr Leu Ala Ala Ala Asn Ser Cys Phe Asn Pro Phe Leu
        275                 280                 285

Tyr Tyr Phe Ala Gly Glu Asn Phe Lys Ala Arg Leu Arg Ala Ile Phe
    290                 295                 300

Ser Lys Asp His Leu
305

<210> SEQ ID NO 23
<211> LENGTH: 37
<212> TYPE: DNA
<213> ORGANISM: Artificial Sequence
<220> FEATURE:
<223> OTHER INFORMATION: artificially synthesized primer sequence

<400> SEQUENCE: 23
gggtctagaa tggagagaaa acttatgtcc ttacttc                              37
```

-continued

```
<210> SEQ ID NO 24
<211> LENGTH: 40
<212> TYPE: DNA
<213> ORGANISM: Artificial Sequence
<220> FEATURE:
<223> OTHER INFORMATION: artifically synthesized primer sequence

<400> SEQUENCE: 24
ccctctagac tattacactc tcgtttcctt tttcagccac                              40
```